United States Patent
Shafer

(10) Patent No.: US 7,769,442 B2
(45) Date of Patent: *Aug. 3, 2010

(54) DEVICE AND METHOD FOR INHIBITING RELEASE OF PRO-INFLAMMATORY MEDIATOR

(75) Inventor: Lisa Lynn Shafer, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 933 days.

This patent is subject to a terminal disclaimer.

(21) Appl. No.: 11/467,963

(22) Filed: Aug. 29, 2006

(65) Prior Publication Data

US 2006/0287678 A1 Dec. 21, 2006

Related U.S. Application Data

(63) Continuation of application No. 10/820,937, filed on Apr. 8, 2004, now abandoned.

(60) Provisional application No. 60/507,855, filed on Oct. 1, 2003.

(51) Int. Cl.
*A61N 1/00* (2006.01)

(52) U.S. Cl. .......................................................... 607/2

(58) Field of Classification Search ............... 607/1–3, 607/39–46, 48, 72
See application file for complete search history.

(56) References Cited

U.S. PATENT DOCUMENTS

| 3,902,501 A | 9/1975 | Citron et al. |
| 4,106,512 A | 8/1978 | Bisping |
| 4,476,868 A | 10/1984 | Thompson |
| 4,566,063 A | 1/1986 | Zolnowsky et al. |
| 4,692,147 A | 9/1987 | Duggan |
| 5,199,428 A | 4/1993 | Obel et al. |
| 5,207,218 A | 5/1993 | Carpentier et al. |
| 5,300,107 A | 4/1994 | Stokes et al. |
| 5,330,507 A | 7/1994 | Schwartz |
| 5,344,438 A | 9/1994 | Testerman et al. |
| 5,501,703 A | 3/1996 | Holsheimer et al. |
| 5,640,764 A | 6/1997 | Strojnik |
| 5,643,330 A | 7/1997 | Holsheimer et al. |
| 5,660,163 A | 8/1997 | Schulman et al. |
| 5,750,926 A | 5/1998 | Schulman et al. |
| 5,791,344 A | 8/1998 | Schulman et al. |
| 5,800,465 A | 9/1998 | Thompson et al. |
| 5,876,425 A | 3/1999 | Gord et al. |

(Continued)

OTHER PUBLICATIONS

Van Horne, et al., Multichannel Semiconductor-Based Electrodes for In Vivo Electrochemical and Electrophysiological Studies in Rat CNS, Neuroscience Letters,1990, 249-252, 120.

*Primary Examiner*—Kennedy J Schaetzle
*Assistant Examiner*—Jessica Sarcione
(74) *Attorney, Agent, or Firm*—Campbell Nelson Whipps LLC

(57) ABSTRACT

Stimulation of one or more neurons of the sympathetic nervous system, including the splenic nerve, is provided to attenuate an immune response, including an inflammatory immune response. Devices such as pulse generators and drug pumps may be used to stimulate the sympathetic nervous system to attenuate an immune response. Systems optionally having one or more sensors and operator instructions may also be used. In specific examples, stimulation of the splenic nerve of pigs with a pulse generator is shown to be safe and effective in attenuating a lipopolysaccharide-induced immune response.

20 Claims, 26 Drawing Sheets

U.S. PATENT DOCUMENTS

| | | |
|---|---|---|
| 5,917,346 A | 6/1999 | Gord |
| 5,957,958 A | 9/1999 | Schulman et al. |
| 5,999,848 A | 12/1999 | Gord et al. |
| 6,043,437 A | 3/2000 | Schulman et al. |
| 6,058,331 A * | 5/2000 | King .......................... 607/62 |
| 6,088,608 A | 7/2000 | Schulman et al. |
| 6,185,452 B1 | 2/2001 | Schulman et al. |
| 6,259,937 B1 | 7/2001 | Schulman et al. |
| 6,421,566 B1 | 7/2002 | Holsheimer |
| 6,610,713 B2 | 8/2003 | Tracey |
| 6,735,475 B1 * | 5/2004 | Whitehurst et al. ........... 607/46 |
| 6,885,888 B2 | 4/2005 | Rezai |
| 6,971,393 B1 | 12/2005 | Mamo et al. |
| 7,418,292 B2 * | 8/2008 | Shafer .......................... 607/2 |
| 2002/0116030 A1 | 8/2002 | Rezai |
| 2003/0045909 A1 | 3/2003 | Gross et al. |
| 2003/0045919 A1 | 3/2003 | Swoyer et al. |
| 2004/0220552 A1 | 11/2004 | Heruth et al. |
| 2004/0220621 A1 * | 11/2004 | Zhou et al. ..................... 607/2 |
| 2004/0249416 A1 * | 12/2004 | Yun et al. ...................... 607/2 |
| 2005/0075701 A1 | 4/2005 | Shafer |

\* cited by examiner

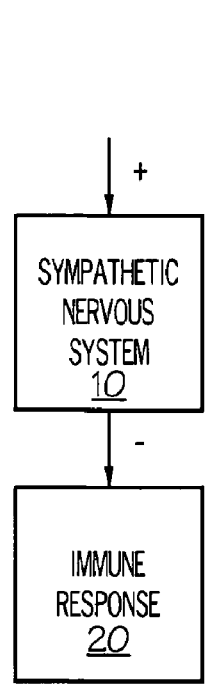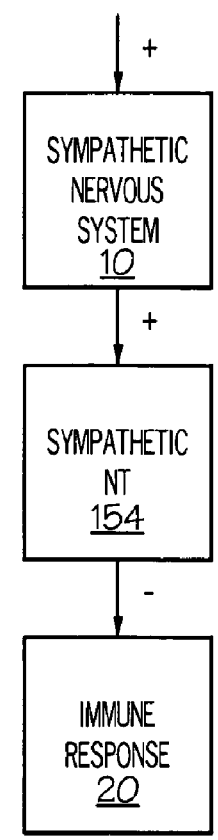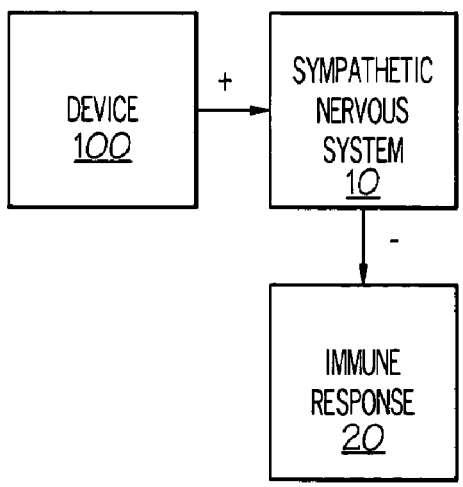
FIG. 1
FIG. 3
FIG. 4

IMPLANT HARDWARE

IMPLANTABLE NEUROSTIMULATOR:
    MEDTRONIC ITREL3 (MODEL 7425G)

NEUROMUSCULAR LEADS (2):
    MEDTRONIC MODEL 4351

STIMULATION PARAMETERS

| | |
|---|---|
| AMPLITUDE: | 5 milliamps |
| PULSE WIDTH: | 330 μsec |
| RATE: | 14Hz |
| CYCLE ON TIME: | 0.1 sec |
| CYCLE OFF TIME: | 5.0 sec |

US 7,769,442 B2

DEVICE AND METHOD FOR INHIBITING RELEASE OF PRO-INFLAMMATORY MEDIATOR

CROSS REFERENCE TO RELATED APPLICATIONS

This application is a continuation application of U.S. patent application Ser. No. 10/820,937, filed Apr. 8, 2004, now abandoned, and claims priority to U.S. Provisional Application No. 60/507,855, filed Oct. 1, 2003, which applications are hereby incorporated herein by reference in their entirety.

FIELD OF THE INVENTION

The invention relates to medical devices and methods for modulating neurons and modulating an immune response.

BACKGROUND

The use of electrical stimulation to attenuate an immune response has only recently been described and has been limited to stimulation of a parasympathetic nerve. U.S. Pat. No. 6,610,713 (Tracey) demonstrated that stimulation of the parasympathetic vagus nerve prior to bacterial challenge resulted in a weakened systemic inflammatory response and was associated with greater survivability.

While intriguing, stimulation of the vagus nerve to attenuate an immune response presents several concerns. Because the vagus nerve is comprised predominantly of afferent fibers, stimulation of the vagus nerve can produce undesired, non-specific CNS effects. While U.S. Pat. No. 6,610,713 discusses selective stimulation of the efferent vagus, selective efferent stimulation will be difficult to achieve in a predominantly afferent nerve such as the vagus. Further, the vagus nerve is a "wandering" nerve that innervates several tissues in addition to the spleen, including the heart, liver and gastrointestinal tract. Accordingly, stimulation of the vagus nerve to attenuate an immune response may result in many undesired and non-specific effects.

Further, due to the complex mechanisms underlying control of an immune response, stimulation of the vagus nerve may not produce a complete or effective attenuation of a systemic inflammatory response. U.S. Pat. No. 6,610,713 suggested that the weakened systemic inflammatory response following vagus nerve stimulation was due to inhibition of pro-inflammatory cytokines through a nicotinic cholinergic receptor-mediated response. However, the parasympathetic cholinergic aspect of regulation of an inflammatory response is only one aspect of such regulation. For example, the sympathetic noradrenergic nervous system may also play a role in regulating an inflammatory immune response.

Like the parasympathetic nervous system, the sympathetic nervous system innervates the spleen, which is a major lymphoid organ. The efferent fibers of the sympathetic splenic nerve include noradrenergic neurons. Some main targets of noradrenergic innervation of the spleen include immature and mature immune cells, such as T lymphocytes, macrophages, mast cells, and plasma cells. In a normal healthy individual, the immune cells maintain a homeostasis with regard to the various factors released by the immune cells. Dysfunction of these cell types can lead to increased release of pro-inflammatory cytokines resulting in inflammation and an excessive immune response. Similarly, dysfunction in these cell types can lead to a suppressed immune response such as that observed in immunocompromised patients.

Noradrenergic agonists appear to play a role in the regulation of such cell-types. For example, norepinephrine and b-adrenergic agonists have been shown to be involved in the elimination of bacteria and may act as endogenous regulators of cytokine production in sepsis. In addition, enhanced norepinephrine levels and b-adrenergic receptor activation can decrease pro-inflammatory cytokine levels, increase anti-inflammatory cytokine levels, and alter immune effector functions during bacterial infection.

The use of electrical stimulation of a nerve or tissue associated with the sympathetic nervous system to control an immune response in vivo has not previously been described. However, as presented herein, stimulation of the sympathetic nervous system, particularly the splenic nerve, the fibers of which are predominantly efferent, may serve to attenuate an inflammatory immune response while providing less potentially undesired effects than would stimulation of the parasympathetic nervous system, particularly the vagus nerve. Furthermore, inhibition of the sympathetic nervous system may be used to strengthen an immune response when the endogenous immune response is not sufficient. Taken as a whole, varying the output of the sympathetic nervous system can serve to modulate an immune response for a desired effect thereby allowing for fine adjustments.

SUMMARY OF THE INVENTION

An embodiment of the invention provides a system for attenuating an inflammatory immune response. The system includes a device capable of stimulating a sympathetic nervous system of a subject. In an embodiment, the system includes (a) a pulse generator adapted for stimulation of the sympathetic nervous system and (b) one or more leads connected to the pulse generator and adapted to being positioned to apply a stimulus to the sympathetic nervous system. In an embodiment, the one or more leads are adapted to being positioned to apply a stimulus to the splenic nerve. The system may also include operator instructions for how to operate the device and/or system. For example, the system may include operator instructions indicating that the device or system may be used for purposes of stimulating a neuron associated with the sympathetic nervous system to attenuate an immune response, instructions regarding parameters for setting a pulse generator to stimulate the sympathetic nervous system, instructions for how to position a lead to stimulate the sympathetic nervous system, etc. The system may also include a sensor. The senor may be coupled to a stimulator to adjust one or more stimulation parameter. The sensor may be capable of detecting a dysfunctional immune or sickness response, detecting whether a neuron has been stimulated or whether an immune response has been attenuated or enhanced, and the like.

In an embodiment, the invention provides a method for attenuating an immune response through stimulation of the sympathetic nervous system. The immune response may be an inflammatory immune response. The sympathetic nervous system can be stimulated electrically with, for example, a pulse generator. In an embodiment, stimulation of the sympathetic nervous system includes stimulation of the splenic nerve.

In an embodiment, the invention provides a method for enhancing an immune response through modulation of the sympathetic nervous system.

In another embodiment, the invention provides a method for modulating an immune response through the combined stimulation of the parasympathetic and sympathetic nervous systems. The immune response may be an inflammatory immune response or an immunosuppressive response. Both the parasympathetic and sympathetic nervous systems may be stimulated electrically with, for example, a pulse generator. In an embodiment, stimulation of the parasympathetic nervous system may include stimulation of the vagus nerve. In an embodiment, stimulation of the sympathetic nervous system may include stimulation of the splenic nerve. The stimulation may be delivered at the same time or at alternating times to allow for finer control of an immune response.

In another embodiment, the invention is directed to a computer-readable medium comprising program instructions. The program instructions cause a programmable processor to quantify one or more conditions of a subject to establish a health state of the subject, the one or more condition being associated with an immune response; instruct a medical device to provide a stimulatory signal having stimulation parameters to a neuron; determine whether the health state of the subject improved based on changes in one or more of the one or more conditions; and modify the stimulation parameters based the determination of whether the health state of the subject improved. A medical device may comprise the computer-readable medium.

The invention can provide a number of advantages. For example, by stimulating the sympathetic nervous system, which innervates all primary and secondary lymphoid organs, the invention provides for great flexibility for controlling an inflammatory immune response. By stimulating one or more sympathetic nerves that innervate one or more lymphoid organs, an inflammatory immune response can be attenuated at one or more levels. In addition, the invention provides for greater specificity with reduced potential undesired, non-specific effects. For example, stimulating the splenic nerve, which is comprised primarily of efferent fibers, can attenuate an immune response while minimizing direct CNS effects due to the stimulation. Other advantages will also be evident based on the disclosure herein.

BRIEF DESCRIPTION OF THE DRAWINGS

FIG. 1 is a diagrammatic illustration of stimulation of a sympathetic nervous system attenuating an immune response;

FIG. 3 is a diagrammatic illustration of stimulation of a sympathetic nervous system producing sympathetic neurotransmitters attenuating an immune response;

FIG. 4 is a diagrammatic illustration of a device stimulating a sympathetic nervous system attenuating an immune response;

The drawings are not necessarily to scale. Like numbers refer to like parts or steps throughout the drawings.

DETAILED DESCRIPTION

Figure 2:
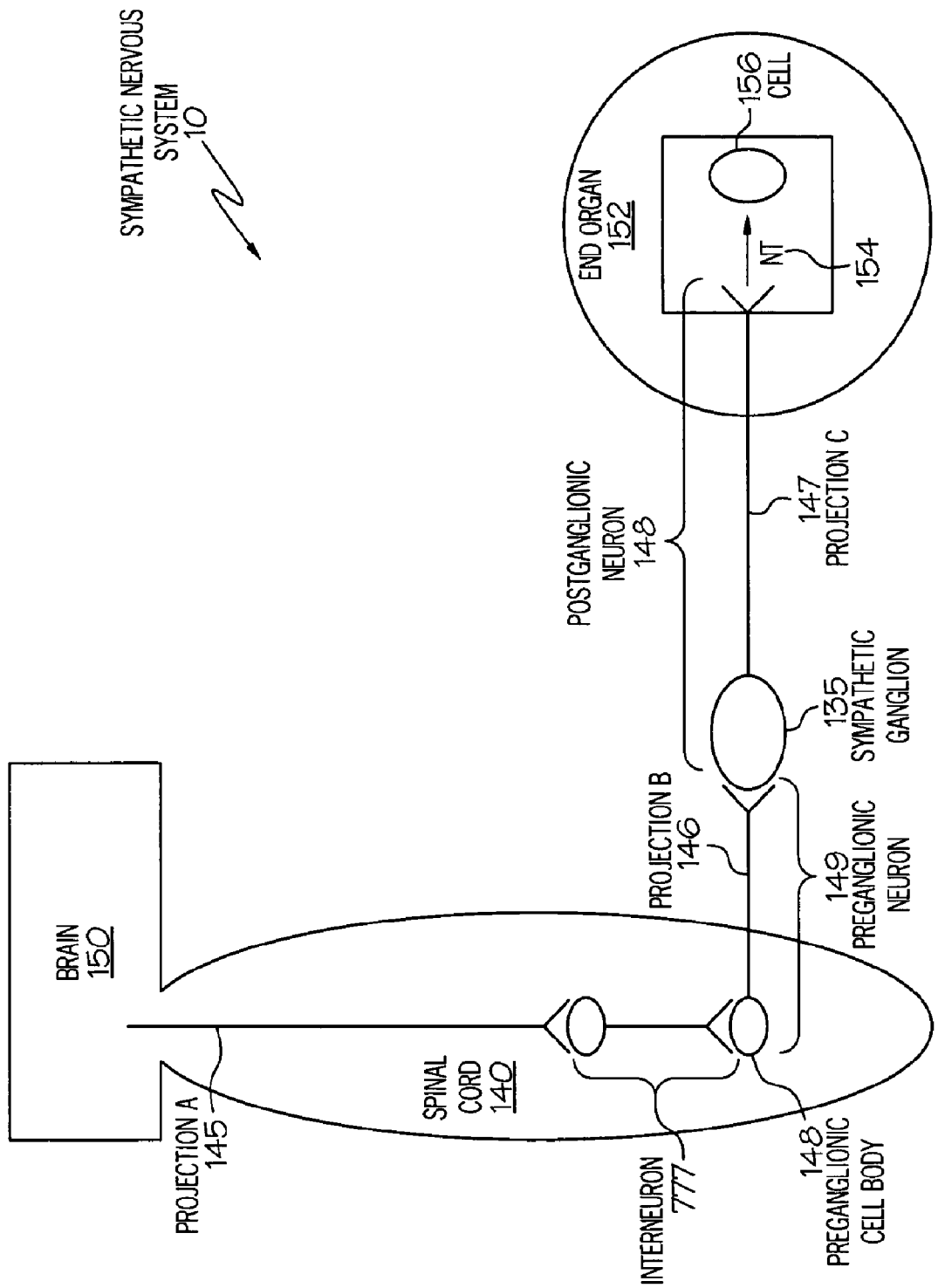
FIG. 2 is a diagrammatic illustration of a sympathetic nervous system.

In the following descriptions, reference is made to the accompanying drawings that form a part hereof, and in which are shown by way of illustration several specific embodiments of the invention. It is to be understood that other embodiments of the present invention are contemplated and may be made without departing from the scope or spirit of the present invention. The following detailed description, therefore, is not to be taken in a limiting sense.

Definitions

All scientific and technical terms used in this application have meanings commonly used in the art unless otherwise specified. The definitions provided herein are to facilitate understanding of certain terms used frequently herein and are not meant to limit the scope of the present disclosure.

As used herein, "subject" means a living being having an autonomic nervous system. "Subject" includes mammals such as mice, rats, pigs, cats, dogs, horses, non-human primates and humans. "Autonomic nervous system" collectively refers to the sympathetic and parasympathetic nervous system.

As used herein, "mediator" of an immune response means a molecule that affects an immune response in a subject and includes proinflammatory and anti-inflammatory cytokines and chemokines and their respective receptors, as well as signal transduction molecules involved in transmitting a signal associated with interaction of a cytokine or chemokine with a receptor.

Attenuation of an Immune Response

FIG. 1 illustrates an embodiment of the invention, where a sympathetic nervous system 10 of a subject is stimulated to attenuate an immune response 20. It is understood that any means capable of stimulating a sympathetic nervous system 10, or one or more neurons thereof, may be employed. As used herein, "attenuating an immune response" 20 means to reduce the ability of a subject to produce an immune response 20, reduce the ability of a subject to produce mediators of an immune response 20, increase the ability of a subject to produce an anti-immune response, and/or increase the ability of a subject to produce mediators of an anti-immune response. Attenuation of an immune response 20 may be detected by measuring a reduction in a deleterious characteristic associated with an immune response 20, a reduction in a quantified symptom of a deleterious characteristic, disease, and/or disorder associated with an immune response 20, a reduction in the level of a mediator of an immune response 20, an increase in the level of a mediator of an anti-immune response, and the like, or a combination thereof.

In an embodiment, the immune response 20 may be an inflammatory immune response 20. An inflammatory immune response 20 can be mediated by an inflammatory cytokine cascade and can be alleviated by an anti-inflammatory cytokine cascade. Attenuation of an inflammatory immune response 20 may be detected by measuring a decrease in one or more proinflammatory cytokines. Non-limiting examples of proinflammatory cytokines include tumor necrosis factor (TNF; also known as TNFα or cachectin), interleukin (IL)-1α, IL-1β, IL-2; IL-5, IL-6, IL-8, IL-15, IL-18, interferon γ (IFN-γ); platelet-activating factor (PAF), thromboxane; soluble adhesion molecules; vasoactive neuropeptides; phospholipase A2; plasminogen activator inhibitor (PAI-1); free radical generation; neopterin; CD14; prostacyclin; neutrophil elastase; protein kinase; monocyte chemotactic proteins 1 and 2 (MCP-1, MCP-2); macrophage migration inhibitory factor (MIF), high mobility group box protein 1 (HMGB-1), and other known factors. Attenuation of an inflammatory immune response may also be detected by measuring an increase in one or more anti-inflammatory cytokines. Non-limiting examples of anti-inflammatory cytokines include IL-4, IL-10, IL-17, IL-13, IL-1 alpha, and TNFalpha receptor. It will be recognized that some of proinflammatory cytokines may act as anti-inflammatory cytokines in certain circumstances, and vice-versa. Such cytokines are typically referred to as plieotropic cytokines. Attenuation of an inflammatory response may also be detected by measuring changes (baseline versus during therapy delivery, a first point in therapy versus a second point in therapy, etc.) in the presence of other factors involved in an immune response. Non-limiting examples of such other factors include TGF, PDGF, VEGF, EGF, FGF, I-CAM, nitric oxide, and other known factors. In addition, an attenuated immune response may be detected by changes in chemokines, such as 6cKine and MIP3beta, and chemokine receptors, including CCR7 receptor. Further, attenuation of an immune response may be measured by changes in immune cell population (upregulated Langerhans cells, dendritic cells, lymphocytes), or immune cell surface co-stimulatory molecules (Major Histocompatibility, CD80, CD86, CD28, CD40). Attenuation of an inflammatory response may also be detected by measuring changes in other factors involved in the inflammatory cascade, for example in the signal transduction cascades including factors such as NFκ-B, Egr-1, Smads, toll-like receptors, and MAP kinases. Attenuation of an immune response may also be detected by a change in the presence of, or the clearance of, an exogenous antigen believed to have caused an inflammatory response, such as e.g. a bacteria, a virus, or a fungus. Further, cell types involved in an immune response, such as Langerhans cells, dendritic cells, T lymphocytes, and B lymphocytes may be detected. In addition, cell surface molecules involved in an immune response, such as major histocompatibility complex (MHC), CD80, CD86, CD28, and CD40 may be detected.

Attenuation of an inflammatory immune response 20 includes attenuation of a deleterious characteristic of a disorder and/or disease state associated with a heightened inflammatory immune response 20. Deleterious characteristics include inflammation and apoptosis. Disorders or disease states associated with an inflammatory immune response 20 are described in U.S. Pat. No. 6,610,713 and include disorders characterized by both localized and systemic reactions, including, diseases involving the gastrointestinal tract and associated tissues (such as appendicitis, peptic, gastric and duodenal ulcers, peritonitis, pancreatitis, ulcerative, pseudomembranous, acute and ischemic colitis, inflammatory bowel disease, diverticulitis, epiglottitis, achalasia, cholangitis, coeliac disease, cholecystitis, hepatitis, Crohn's disease, enteritis, and Whipple's disease); systemic or local inflammatory diseases and conditions (such as asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, and sarcoidosis); diseases involving the urogential system and associated tissues (such as septic abortion, epididymitis, vaginitis, prostatitis and urethritis); diseases involving the respiratory system and associated tissues (such as bronchitis, emphysema, rhinitis, cystic fibrosis, adult respiratory distress syndrome, pneumonitis, pneumoultramicroscopicsilicovolcanoconiosis, alvealitis, bronchiolitis, pharyngitis, pleurisy, and sinusitis); diseases arising from infection by various viruses (such as influenza, respiratory syncytial virus, HIV, hepatitis B virus, hepatitis C virus and herpes), bacteria (such as disseminated bacteremia, Dengue fever), fungi (such as candidiasis) and protozoal and multicellular parasites (such as malaria, filariasis, amebiasis, and hydatid cysts); dermatological diseases and conditions of the skin (such as burns, dermatitis, dermatomyositis, sunburn, urticaria warts, and wheals); diseases involving the cardiovascular system and associated tissues (such as vasulitis, angiitis, endocarditis, arteritis, atherosclerosis, thrombophlebitis, pericarditis, myocarditis, myocardial ischemia, congestive heart failure, periarteritis nodosa, and rheumatic fever); diseases involving the central or peripheral nervous system and associated tissues (such as Alzheimer's disease, meningitis, encephalitis, multiple sclerosis, cerebral infarction, cerebral embolism, Guillame-Barre syndrome, neuritis, neuralgia, spinal cord injury, paralysis, and uveitis); diseases of the bones, joints, muscles and connective tissues (such as the various arthritides and arthralgias, osteomyelitis, fasciitis, Paget's disease, gout, periodontal disease, rheumatoid arthritis, and synovitis); other autoimmune and inflammatory disorders (such as myasthenia gravis, thryoiditis, systemic lupus erythematosus, Goodpasture's syndrome, Behcets's syndrome, allograft rejection, graft-versus-host disease, Type I diabetes, ankylosing spondylitis, Berger's disease, diabetes including Type I diabetes, ankylosing spondylitis, Berger's disease, and Retier's syndrome); as well as various cancers, tumors and proliferative disorders (such as Hodgkins disease), nosicomal infection; and, in any case the inflammatory or immune host response to any primary disease.

Other conditions associated with immune or inflammatory response include injury to nerves or other tissue and pain associated with nerve or other tissue. Injury may be due to a physical, chemical or mechanical trauma. Non-limiting examples of injury include acute trauma, burn, and whiplash. Conditions associated with a particular organ such as eye or ear may also include an immune or inflammatory response.

Any method for measuring the level of a cytokine or chemokine in a subject may be used to determine whether an inflammatory immune response 20 has been attenuated. Several methods are known and include commercially available kits. A cytokine or chemokine may be directly detected. Alternatively, the presence or amount of a nucleic acid, such as a polyribonucleotide, encoding a polypeptide described herein may serve as a measure of the presence or amount of the polypeptide. Thus, it will be understood that detecting the presence or amount of a polypeptide will include detecting the presence or amount of a polynucleotide encoding the polypeptide.

Any method for measuring a deleterious characteristic, disorder and/or disease state associated with a heightened inflammatory immune response may be used. Several methods are known and include determining the level of inflammation in a subject, determining the extent of apoptosis in a subject, determining physiological changes characteristic of a particular disease state, and determining a subject's white blood cell count. Inflammation may be measured in vitro or in vivo by analysis of inflammatory markers in the blood and fluorescence and histological evidence and physiological responses such as body temperature. Apoptosis may be measured by dye uptake and circulating levels of apoptosis markers, and tissue biopsy. These and other known methods may be used to measure an inflammatory immune response.

Further, any symptom associated with a deleterious characteristic, disease, or disorder of an inflammatory immune response 20 may be used to determine whether an inflammatory immune response 20 has been attenuated. A symptom may be quantified either objectively or subjectively. Non-limiting examples of objective measures include decreased swelling, decreased flushing, changes in ECG, EKG, changes in measures of total health, changes in response to pain tests, and decreased body temperature. Other objective measures of improvement in disorders or disease states associated with a heightened immune response 20 are known and may be used to determine efficacy of the various embodiments of the invention. Subjective measures, e.g., the subject's perception of the one or more symptom of an inflammatory immune response may be quantified in any know manner. For example, the subject may rank their perceived severity of the symptom on base on a numerical scale. The scale can be from, 1 to 2, from 1 to 3, from 1 to 4, from 1 to 5, from 1 to 10, etc.

Sympathetic Nervous System

FIG. 1 illustrates an embodiment of the invention, where a sympathetic nervous system 10 of a subject is stimulated to attenuate an immune response 20. The invention provides, in various embodiments, devices and methods for stimulating a sympathetic nervous system 10 of a subject to attenuate an immune response 20. Sympathetic nervous system 10 is used herein in its broadest sense and includes stimulation of one or more neurons associated with the sympathetic nervous system.

As shown in FIG. 2, neurons associated with the sympathetic nervous system 10 include projections in the spinal cord 145 that originate from the brain to interneurons 777 or to preganglionic neurons 149 (not shown), interneurons 777, preganglionic neurons 149 and postganglionic neurons 148. Projections a 145 from the brain 150 including brain stem, midbrain and forebrain to preganglionic sympathetic neurons 149 or interneurons 777 (it will be recognized that one or more interneurons 777 may be involved in relaying information from brain projections a 145 to a preganglionic neuron 149) of the spinal cord 140 include projections a 145 from brain 150 areas such as the paraventricular nucleus of the hypothalamus, rostral ventrolateral medulla, ventromedial medulla, and caudal raphe nucleus. In an embodiment of the invention, one or more of such brain 150 areas may be stimulated to attenuate an immune response 20 in a subject. The preganglionic cell bodies 148 of the sympathetic nerves and associated interneurons 777 generally reside within the intermediolateral cell column of the lateral horn of the spinal cord 140 at C1-S5. In an embodiment of the invention, neurons in such regions of the spinal cord 140 may be stimulated to attenuate an immune response 20. Generally, preganglionic cell bodies 148 send projections b 146 that exit the spinal cord 140 through the ventral roots to synapse with postganglionic neurons 148 in ganglia 135. Examples of ganglia 135 include inferior mesenteric, superior mesenteric, celiac, submandibular, otic, and pterygopalatine ganglia. Postganglionic nerves 148 send projections c 147 that typically follow the vasculature to innervate end organs 152. Postganglionic sympathetic neurons 148 can be stimulated directly by, for example, stimulating the ganglia 135 or stimulating the projection c 147 of the neuron. A postganglionic neuron 148 can be stimulated indirectly by, for example stimulating a preganglionic neuron 149 that synapses with the postganglionic neuron 148 or stimulating any of its higher origins. Further, stimulation of tissue of an end organ 152 may stimulate a postganglionic sympathetic neuron 148. Generally, stimulation of a postganglionic sympathetic neuron will increase the likelihood that neurotransmitter 154 will be released from the nerve terminal of the neuron 148. However, it will be understood that neurotransmitter 154 may also be released nonsynaptically, at any point along the neuron cell body or projections. The neurotransmitter 154 released from the postganglionic neuron 148 may interact with one or more cells 156 of, within, or near the end organ 152. Non-limiting examples of neurotransmitters 154 released from postganglionic sympathetic neurons 148 include epinephrine, norepinephrine, substance P, neuropeptide Y, and dopamine.

From preganglionic cell bodies 148 residing in the spinal cord 140 sympathetic projections b and c, 146 and 147, are sent to innervate various end organs 152. For example, connections arising from sympathetic neurons residing at C1-C4 innervate eyes, lacrimal gland, parotid gland, and submandibular gland; C1-T4 innervate thymus and thyroid gland; T5-T9 innervate stomach, liver, gallbladder, bile ducts, pancreas, and adrenal glands; T10-T12 innervate adrenal glands and kidneys; T10-L2 innervate intestines; L1-L5 innervate distal colon; S2-S5 innervate bladder and genitalia.

As shown in FIG. 3, these and other sympathetic neurotransmitters 154 may be involved in attenuating an immune response 20 in a subject following stimulation of one or more neuron associated with the sympathetic nervous system 10.

Accordingly, in various embodiments the invention provides systems and methods to increase sympathetic neurotransmitter 154 output from a sympathetic neuron by stimulating one or more sympathetic neuron. The invention also provides in various embodiments systems and methods for attenuating an immune response 20 by increasing the level of a sympathetic neurotransmitter 154 in a subject. Furthermore, embodiments of the invention provide systems and methods for enhancing an immune function.

Stimulation of Sympathetic Nervous System

The invention provides, in various embodiments, devices and methods for stimulating the sympathetic nervous system 10. As used herein, "stimulating the sympathetic nervous system 10" means to increase the likelihood that one or more neurons associated with the sympathetic nervous system 10 will undergo an action potential. A sympathetic neuron can be stimulated by applying a neurostimulatory signal to the neuron. Thus, any stimulation signal that increases the likelihood that a neuron will undergo an action potential is considered neurostimulatory according to various embodiments of the invention. In some embodiments, the neurostimulatory signal is sufficient to induce the neuron to undergo an action potential. A stimulatory signal may be applied to a sympathetic neuron or a population of neurons within a given region of the sympathetic nervous system 10, anywhere along the sympathetic nervous system pathway. Cell bodies, dendritic projections, or axonal projections may be stimulated. Indirect stimulation of a sympathetic nervous system 10 by stimulating tissue that can in turn stimulate the sympathetic nervous system 10 is also contemplated by various embodiments of the invention. For example, stimulation of a stomach, pancreas, liver, gall bladder and/or adrenal medulla to stimulate a sympathetic neuron are envisioned.

In an embodiment, one or more of the stimulated neurons are efferent neurons. Efferent fibers can be stimulated by stimulating an entire sympathetic nerve (i.e., both afferent and efferent nerves) or by isolating efferent nerves and stimulating them directly. The latter method can be accomplished by separating the afferent from the efferent fibers in an area of the nerve where both types of fibers are present. Alternatively, the efferent fiber is stimulated where substantially no afferent fibers are present, for example close to the end organ 152 served by the efferent fibers. The efferent fibers can also be stimulated, e.g., electrically, by stimulating the end organ 152 directly, thus stimulating the efferent fibers that serve that organ 152. In other embodiments, the ganglion 135 or postganglionic neurons 148 of a sympathetic nerve can be stimulated. A sympathetic nerve can also be cut and the distal end can be stimulated, thus only stimulating efferent sympathetic nerve fibers. In the case of the splenic nerve, where approximately 98% of the fibers are efferent, the entire nerve can be stimulated without producing an excessive afferent stimulation.

When it is desired to reduce potential non-specific and/or undesired effects, it may be preferred that either preganglionic 149 or postganglionic 148 neurons are stimulated. Preferably, postganglionic neurons 148 are stimulated. Various postganglionic sympathetic neurons 148 that may be stimulated according to various embodiments of the invention include the splenic nerve, splanchnic nerves, and others named with respect to the tissue that it innervates. It is preferred that the one or more stimulated neuron associated with the sympathetic nervous system include a neuron that innervates the spleen or other lymph organ, such as thymus, bone marrow, lymph nodes, tonsils, and the like. Such neurons include those of the splenic nerve, and the thymic nerve and others that generally exist in larger nerve plexuses.

When an immediate attenuation of an immune response 20 is desired, for example when a subject is undergoing an acute immune response 20 such as may occur with sepsis, acute pancreatitis, myocardial infarction, ischemia/reperfusion injury, systemic inflammatory response syndrome, etc., it may be preferable to directly stimulate an end organ 152 or other tissue which may in turn stimulate one or more sympathetic neuron. Preferably the end organ 152 is a lymph organ, such as spleen, thymus, bone marrow, lymph nodes, tonsils, and the like. Other tissue that may be stimulated to indirectly stimulate one or more neuron associated with the sympathetic nervous system includes the organs within the peritoneal sac such as the pancreas, stomach, intestines, and other tissues such as cardiac tissue or a particular joint area. Preferably, stimulation of the other tissue stimulates a postganglionic sympathetic neuron 148 in an end organ 152 that is a lymph organ.

In some embodiments, a neuron may be stimulated to an extent that is insufficient by itself to induce an action potential, placing the neuron in an activated state where the neuron will be more likely to undergo an action potential in response to endogenous stimuli. In other embodiments, a neuron may be stimulated to an extent that the neuron is induced to undergo an action potential. In such embodiments, the frequency with which the neuron undergoes an action potential may be closely controlled.

Sympathetic neurons can be stimulated according to various embodiments of the invention in a variety of ways, including chemically, with for example a pharmacological agent, mechanically, and electrically. Any means suitable for stimulating a neuron may be used. Non-limiting examples of suitable means include: mechanical means such as a needle, ultrasound, or vibration; any electromagnetic radiation such as infrared, visible or ultraviolet light; heat, or any other energy source. In an embodiment, the sympathetic nervous system is stimulated electrically, using, e.g., a commercial pulse generator, such as Medtronic Model 3625 Test Stimulator or an electric probe or endoscope with probe. Stimulation parameters, whether stimulation is by chemical, pharmacological, and/or mechanical means, can be determined by the skilled artisan for attenuating an immune response.

A stimulation parameter may be varied to achieve a desired result, such as attenuation of an immune response 20. In an embodiment of the invention, the stimulation signal may be varied to adjust the frequency with which a stimulated neuron undergoes an action potential. Such parameters can be readily determined and adjusted by a subject or a health care professional at any time during treatment. In one embodiment of the invention, a neuron will be stimulated such that it undergoes an action potential with a frequency in the range of about 1 Hz to about 120 Hz. In another embodiment, a neuron will be stimulated such that it undergoes an action potential with a frequency in the range of about 5 Hz to about 50 Hz. In yet another embodiment, a neuron will be stimulated such that it undergoes an action potential with a frequency in the range of about 5 Hz to about 20 Hz.

In an embodiment, the splenic nerve is stimulated such that it undergoes action potential with a frequency in the range of about 1 Hz to about 120 Hz. In another embodiment, the splenic nerve will be stimulated such that it undergoes an action potential with a frequency in the range of about 5 Hz to about 50 Hz. In yet another embodiment, the splenic nerve will be stimulated such that it undergoes an action potential with a frequency in the range of about 5 Hz to about 20 Hz.

The splenic nerve may be stimulated directly or indirectly. For example a stimulatory signal may be applied to the splenic neurovascular bundle at one or more locations along the length of the spleen; the splenic neurovascular bundle either proximal or distal to the bifurcation of the splenic artery and vein into upper and lower splenic branches; the periarterial splenic nerve; a substantially fully dissected splenic nerve or nerve bundles, which contains essentially no vascular tissue; the splenic peritoneum; splenic tissue, including a lineal plexus; and/or combinations thereof. Further, to stimulate a neuron of the splenic nerve, a stimulatory signal may also be applied to the celiac plexus surrounding the celiac artery, which consists of fibers derived from the ganglia and the medulla spinalis; celiac ganglia; aorticorenal ganglia, greater thoracic splanchnic nerves; lesser thoracic splanchnic nerves; least thoracic splanchinc nerves; lower thoracic sympathetic trunk ganglia; upper lumbar sympathetic trunk ganglia; preganglionic sympathetic fibers; preganglionic sympathetic fibers of T8-L2; sympathetic trunk ganglia of T8-L2; white ramus communicans of T8-L2; gray ramus communicans of T8-L2; spinal ganglia at T8-L2; ventral root of T8-L2; preganglionic sympathetic fibers of T9; sympathetic trunk ganglion of T9; white ramus communicans of T9; gray ramus communicans of T9; spinal ganglion of T9; ventral root of T9, and/or combinations thereof.

Figure 5A:
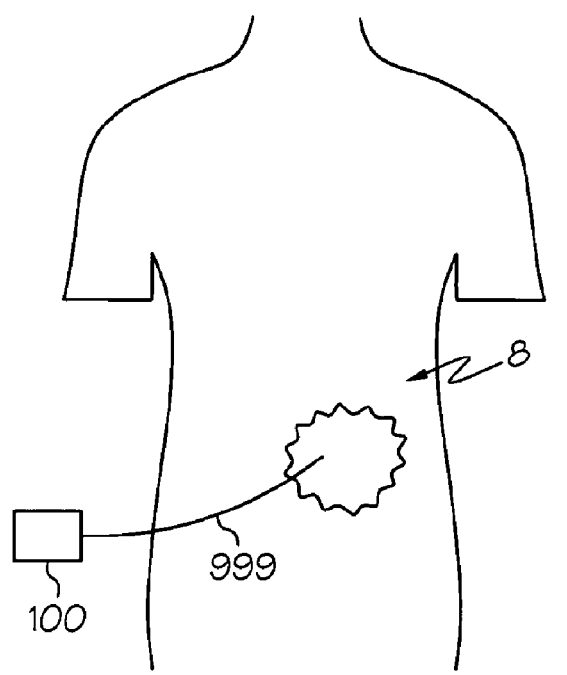
FIGS. 5A and 5B are diagrammatic illustrations of an external system (5A) and an implantable system (5B) capable of stimulating a sympathetic nervous system.
Figure 5B:
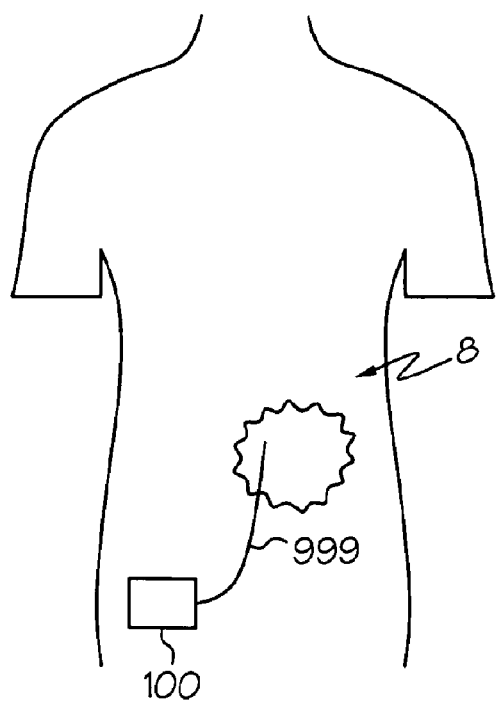

FIG. 4 depicts an embodiment of the invention where a device 100 is adopted to stimulate the sympathetic nervous system 10. A therapy delivery system suitable for stimulating a sympathetic nervous system 10 may comprise a device 100 and a therapy delivery element 999, as shown in FIGS. 5A and 5B. The therapy delivery element 999 comprises a proximal portion coupled to the device 100 and a distal portion adapted to be introduced to a target location 8 of a subject. As shown in FIG. 5A, the device 100 may be external to the subject. As shown in FIG. 5b, the device 100 may be implanted in the subject. Suitable devices 100 for stimulating the sympathetic nervous system or one or more neurons associated therewith include an electric probe, a pulse generator, a drug pump, and the like. Therapeutic element 999 may be, e.g., a lead or a catheter. Suitable implantable devices 100 include an implantable pulse generator, such as Medtronic's Model 7425 Itrel or Model 7427 Synergy, and an implantable drug pump system, such as Medtronic's Synchromed pump and catheter system. A programmer, separate from the therapy delivery system, may be used to modify parameters of the system. Programming may be accomplished with a console remote programmer such as Model 7432 and Model 7457 memory module software or with a hand-held programmer such as an Itrel EZ, available from Medtronic, Inc. of Minneapolis, Minn. Any of a number of suitable programming and telemetry methodologies known in the art may be employed so long as the desired information is transmitted to and from the device 100.

1. Pulse Generator

In an embodiment of the invention, the device 100 may be a pulse generator 101. Any pulse generator 101 capable of stimulating a sympathetic neuron may be used. Typically, pulse generators are coupled to one or more leads, with the leads being positioned to stimulate a sympathetic neuron, either directly or indirectly.

Figure 6A:
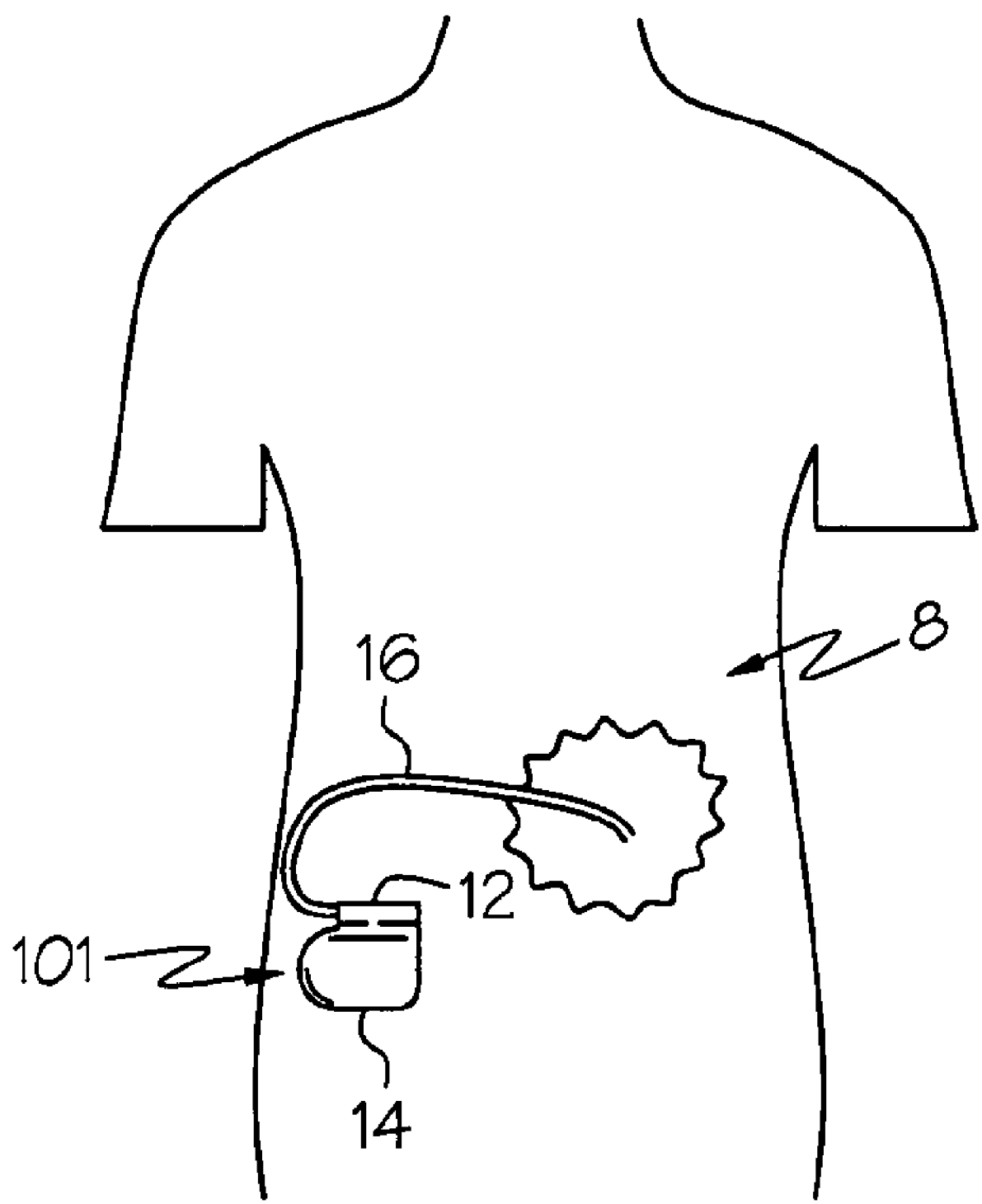
FIG. 6A-6C are diagrammatic illustrations of (A) a suitable arrangement for implanting one embodiment of a electrical stimulation system of the present invention; (B) components of one embodiment of an electric stimulation system of the present invention; and (C) an pulse generator and associated medical electrical leads according to one embodiment of the present invention.

FIG. 6A shows one embodiment of a pulse generator 101 according to the present invention. The pulse generator 101 in FIG. 6A is shown as an implantable pulse generator (IPG) 101 having a lead positioned at or near a desired or target tissue 8. IPG 101 shown in FIG. 6A is an implantable pulse generator system comprising at least one implantable medical electrical lead 16 attached to hermetically sealed enclosure 14. Lead 16 is shown implanted at or near desired or target tissue 8. Enclosure 14 may be formed of a biocompatible material such as an appropriate metal alloy containing titanium. It is important to note that at least one more lead 18 (not shown in the drawings) may be employed in accordance with certain embodiments of the present invention, where multiple target sites are to be stimulated simultaneously or sequentially and/or where such multiple target sites are incapable of being stimulated, or are difficult to stimulate, using a single lead even if the single lead contains multiple stimulation electrodes or arrays of stimulation electrodes. FIG. 6C shows an illustrative IPG and associated medical electrical leads according to one embodiment of the present invention.

Referring now to FIG. 6B and FIGS. 7A through 7F, lead 16 provides electrical stimulation pulses to the desired target sites. Lead 16 and lead 18 may have unipolar electrodes disposed thereon (where enclosure 14 is employed as an indifferent electrode) or may have multipolar, e.g. bipolar, electrodes disposed thereon, where one or more electrodes disposed on a lead are employed as the indifferent electrode. In one embodiment of the present invention, lead 16 extends from lead connector 13, which in turn forms an integral portion of lead extension 15 connected at its proximal end to connector header module 12.

Any suitable material may be used for forming a lead body of leads 16, 18. Examples of suitable materials include polyurethane and silicone. Electrical conductors extending between the proximal and distal ends of leads 16 and 18 for supplying electrical current to the electrodes may be formed of coiled, braided or stranded wires. The wires may be made of any suitable material for carrying electrical current. In an embodiment, the wires comprise an MP35N platinum-iridium alloy. Electrodes 21, 22, 23 and 24 may be ring electrodes, coiled electrodes, electrodes formed from portions of wire, barbs, hooks, spherically-shaped members, helically-shaped members, or may assume any of a number of different structural configurations well known in the art. Electrodes 21, 22, 23 and 24 may be formed of any suitable material. Suitable materials include metals and metal alloys, such as platinum and stainless steel.

The distal portion of lead 16 extends to a target site 8, and may be held in such position by a lead anchor 19. Note that lead anchor 19 may assume any of a number of different structural configurations such one or more suture sleeves, tines, barbs, hooks, a helical screw, tissue in-growth mechanisms, adhesive or glue.

One, two, three, four or more electrodes 21, 22, 23 and 24 may be disposed at the distal end of lead 16 and/or lead 18. Electrodes 21, 22, 23 and 24 are preferably arranged in an axial array, although other types of arrays may be employed such as inter-lead arrays of electrodes between the distal ends of leads 16 and 18 such that nerves or nerve portions 8 disposed between leads 16 and 18 may be stimulated. Electrode configurations, arrays and stimulation patterns and methods similar to those disclosed by Holsheimer in U.S. Pat. No. 6,421,566 entitled "Selective Dorsal Column Stimulation in SCS, Using Conditioning Pulses," U.S. Pat. No. 5,643,330 entitled "Multichannel Apparatus for Epidural Spinal Cord Stimulation" and U.S. Pat. No. 5,501,703 entitled "Multi-channel Apparatus for Epidural Spinal Cord INS," the respective entireties of which are hereby incorporated by reference herein, may also be adapted or modified for use in the present invention. Electrode configurations, arrays, leads, stimulation patterns and methods similar to those disclosed by Thompson in U.S. Pat. No. 5,800,465 entitled "System and Method for Multisite Steering of Cardiac Stimuli," the entirety of which is hereby incorporated by reference herein, may also be adapted or modified for use in the present invention to permit the steering of electrical fields. Thus, although the Figures show certain electrode configurations, other lead locations and electrode configurations are possible and contemplated in the present invention.

Typically, leads 16 and 18 are tunneled subcutaneously between the location of pulse generator 101 and the location or site to be stimulated. Pulse generator 101 is typically implanted in a subcutaneous pocket formed beneath the patient's skin according to methods well known in the art. Further details concerning various methods of implanting a pulse generator 101 and leads 16 and 18 are disclosed in the Medtronic Interstim Therapy Reference Guide published in 1999, the entirety of which is hereby incorporated by reference herein. Other methods of implanting and locating leads 16 and 18 are also contemplated in the present invention.

U.S. patent application Ser. No. 10/004,732 entitled "Implantable Medical Electrical Stimulation Lead Fixation Method and Apparatus", now U.S. Pat. No. 6,999,819, and Ser. No. 09/713,598 entitled "Minimally Invasive Apparatus for Implanting a Sacral Stimulation Lead", now U.S. Pat. No. 6,971,393, to Mamo et al., the respective entireties of which are hereby incorporated by reference herein, describe methods of percutaneously introducing leads 16 and 18 to a desired stimulation site in a patient.

Figure 7A:
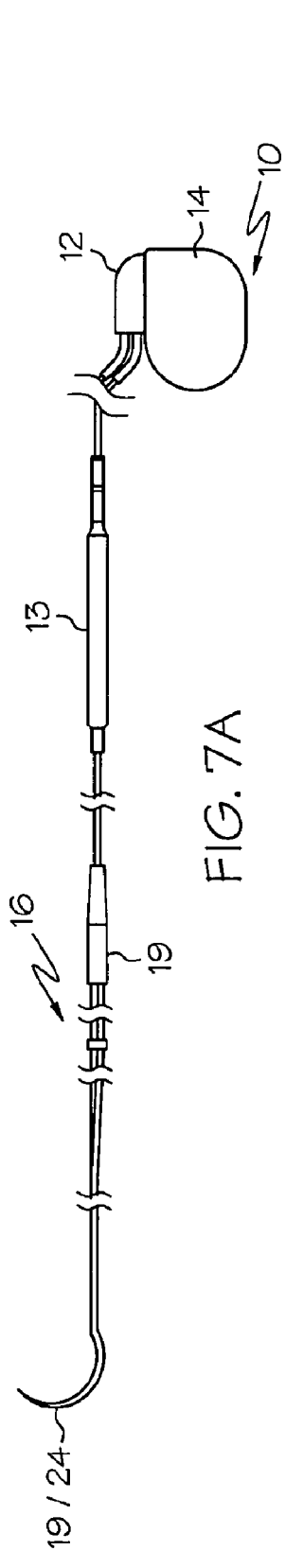
FIG. 7A-7F are diagrammatic illustrations of various embodiments of medical electrical leads suitable for use in various embodiments of a system or method of the present invention.

Some representative examples of leads 16 and 18 include MEDTRONIC stimulation lead model numbers 3080, 3086, 3092, 3487, 3966 and 4350 as described in the MEDTRONIC Instruction for Use Manuals thereof, all hereby incorporated by reference herein, each in its respective entirety. Additional suitable leads include Medtronic's Pisces leads, Resume leads, as described in the MEDTRONIC Instruction for Use Manuals thereof, all hereby incorporated by reference herein, each in its respective entirety; and other custom builds such as cuff electrodes as described in U.S. Pat. No. 5,344,437 (Testerman, Medtronic), which is hereby incorporated by reference in its entirety. See also FIGS. 7B through 7F hereof, which disclose various embodiments of leads 16 and 18 suitable for use in accordance with the present invention. IPG 101 may also be constructed or operate in accordance with at least some portions of the implantable IPGs 101 disclosed in U.S. Pat. No. 5,199,428 to Obel et al., U.S. Pat. No. 5,207,218 to Carpentier et al. or U.S. Pat. No. 5,330,507 to Schwartz, all of which are hereby incorporated by reference herein, each in its respective entirety. Electric probes such as those currently available through Medtronic or a custom built probe may be used. Lead locations and electrode configurations other than those explicitly shown and described here are of course possible and contemplated in the present invention. Lead anchors 19 are shown in FIG. 7C as a series of tines.

Some representative examples of pulse generators 101 include MEDTRONIC implantable electrical IPG model numbers 3023, 7424, 7425 Itrel, 7427 Synergy and Medtronic Model 3625 Test stimulator as described in the Instruction for Use Manuals thereof, all hereby incorporated by reference herein, each in its respective entirety.

Figure 8:
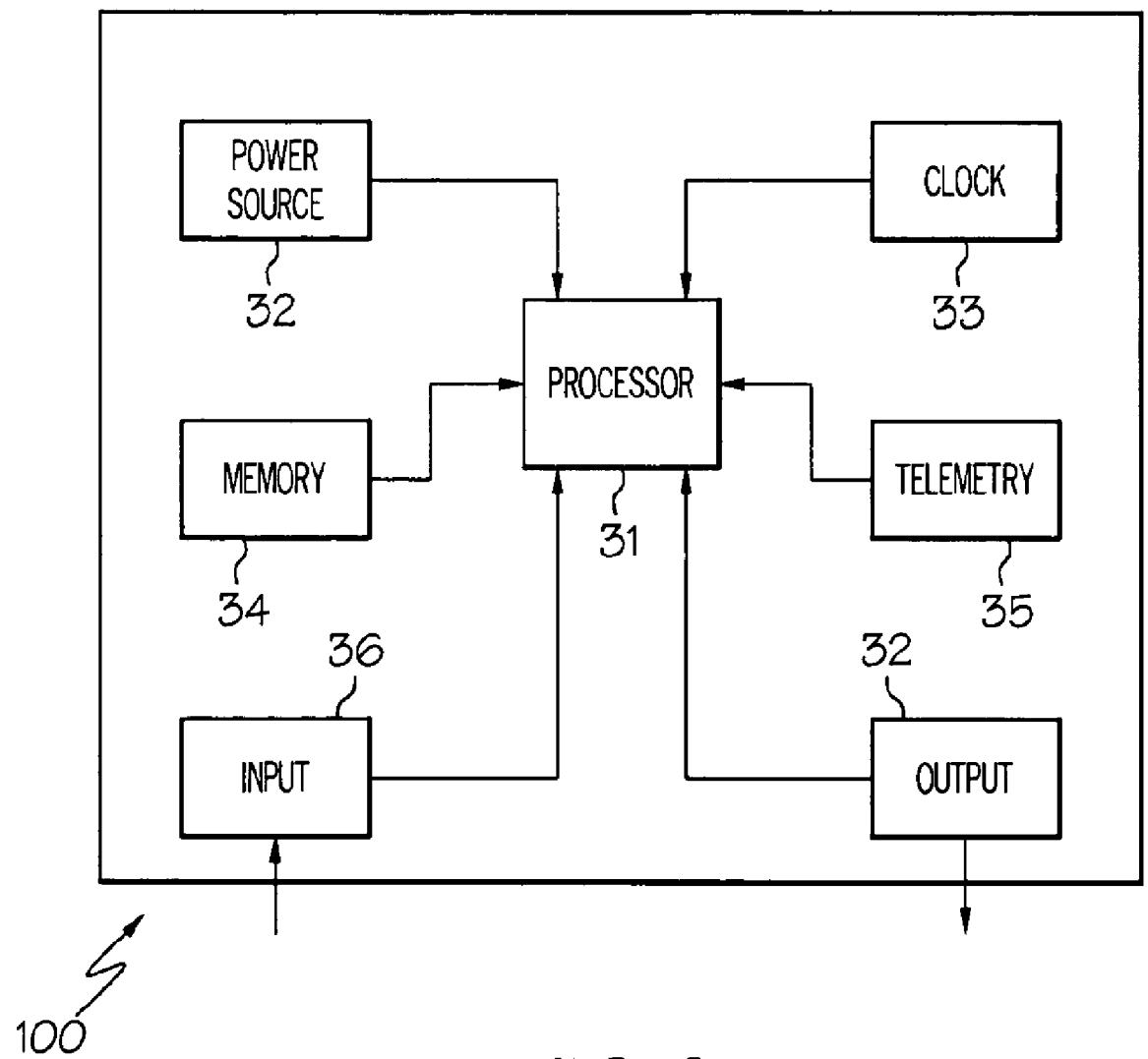
FIG. 8 is diagrammatic illustration of a block diagram of one embodiment of the present invention.

FIG. 8 shows a block diagram illustrating some of constituent components of a device 100 in accordance with an embodiment of the present invention. For the sake of convenience, device 100 in FIG. 8 is discussed with regard to an IPG 101. However, it will be understood that the device 100 the components and interactions described in FIG. 8 may also be applicable to embodiments where device 100 is a drug pump. In the block diagram of FIG. 8, pulse generator 101 has a microprocessor-based architecture. Other architectures of pulse generators 101 are of course contemplated in the present invention, such as the logic or state machine architecture employed in the Medtronic Model Number 3023 INS. For the sake of convenience, those components discussed above and other similar components are not shown in FIG. 8, but it should be understood that such components may be included in an pulse generator 101 according to various embodiments of the invention. Further for the sake of convenience, pulse generator 101 in FIG. 8 is shown with only one lead 16 connected thereto; similar circuitry and connections not shown apply generally to lead 18 and other additional leads not shown in the drawings.

Figure 6B:
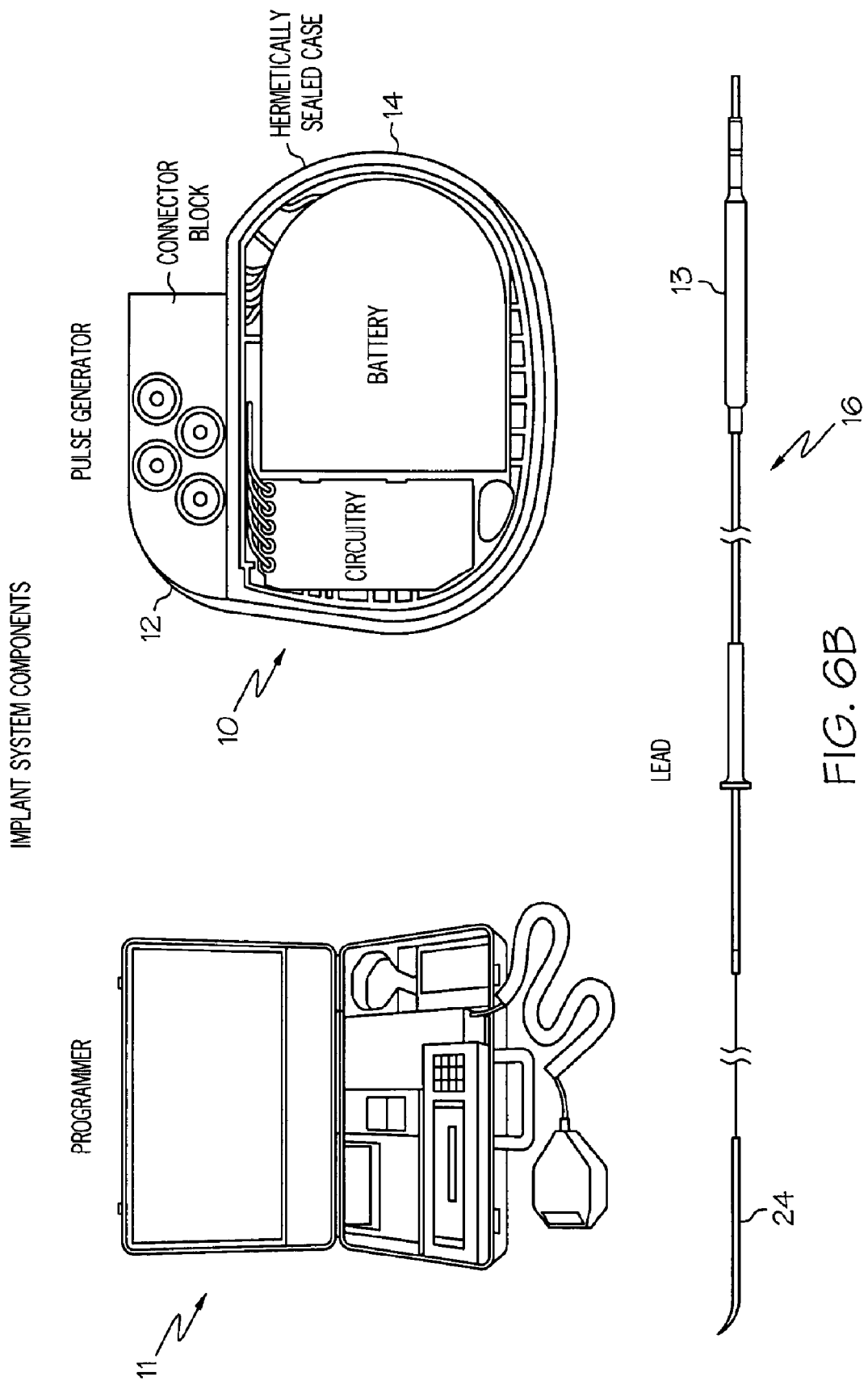
Figure 6C:
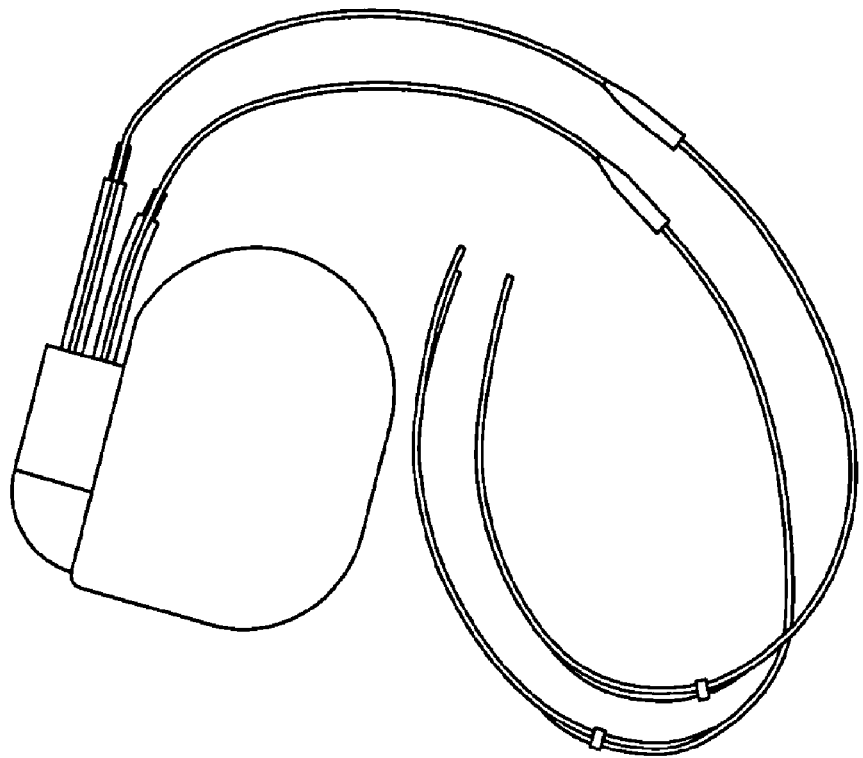

When the pulse generator 101 is an IPG 101, the IPG 101 may be programmable by means of external programming unit 11 shown in FIG. 6b. One such programmer is the commercially available Medtronic Model No. 7432 programmer, which is microprocessor-based and provides a series of encoded signals to IPG 101, typically through a programming head which transmits or telemeters radio-frequency (RF) encoded signals to IPG 101. Another suitable programmer is the commercially available Medtronic Model No. 8840 programmer, which is also microprocessor-based but features a touch control screen. Any of a number of suitable programming and telemetry methodologies known in the art may be employed so long as the desired information is transmitted to and from the implantable electrical IPG 101.

As shown in FIG. 8, IPG 101 may receive input signals via sensor 300 and delivers output stimulation signals to lead 16. IPG 101 most preferably comprises a CPU, processor, controller or micro-processor 31, power source 32 (most preferably a primary or secondary battery), clock 33, memory 34, telemetry circuitry 35, input 36 and output 37. Electrical components shown in FIG. 8 may be powered by an appropriate implantable primary (i.e., non-rechargeable) battery power source 32 or secondary (i.e., rechargeable) battery power source 32. IPG 101 may also contain a battery or capacitor which receives power from outside the body by inductive coupling between an external transmitter and an implanted receiver. For the sake of clarity, the coupling of power source 32 to the various components of IPG 101 is not shown in the Figures. An antenna is connected to processor 31 via a digital controller/timer circuit and data communication bus to permit uplink/downlink telemetry through RF transmitter and receiver telemetry unit 35. By way of example, telemetry unit 35 may correspond to that disclosed in U.S. Pat. No. 4,566,063 issued to Thompson et al. It is generally preferred that the particular programming and telemetry scheme selected permit the entry and storage of electrical stimulation parameters. The specific embodiments of the antenna and other telemetry circuitry presented herein are shown for illustrative purposes only, and are not intended to limit the scope of the present invention.

An output pulse generator provides a stimulation signal to the desired target location 8 through, for example, a coupling capacitor in response to a trigger signal provided by a digital controller/timer circuit, when an externally transmitted stimulation command is received, or when a response to other stored commands is received. By way of example, an output amplifier of the present invention may correspond generally to an output amplifier disclosed in U.S. Pat. No. 4,476,868 to Thompson, hereby incorporated by reference herein in its entirety. The specific embodiments of such an output amplifier are presented for illustrative purposes only, and are not intended to be limiting in respect of the scope of the present invention. The specific embodiments of such circuits may not be critical to practicing some embodiments of the present invention so long as they provide means for generating an appropriate train of stimulating pulses to the desired target location.

In various embodiments of the present invention, pulse generator 101 may be programmably configured to operate so that it varies the rate at which it delivers stimulation signals to the desired target location 8 in response to one or more selected outputs being generated. Pulse generator 101 may further be programmably configured to operate so that it may vary the morphology of the stimulation signals it delivers. Numerous external and implantable electrical pulse generator features and functions not explicitly mentioned herein may be incorporated into pulse generator 101, whether implantable or external, while remaining within the scope of the present invention. Various embodiments of the present invention may be practiced in conjunction with one, two, three or more leads, or in conjunction with one, two, three, four or more electrodes.

It is important to note that leadless embodiments of the present invention are also contemplated, where one or more stimulation and/or sensing electrode capsules or modules are implanted at or near a desired target tissue site, and the capsules or modules deliver electrical stimuli directly to the site using a preprogrammed stimulation regime, and/or the capsules or modules sense electrical or other pertinent signals. Such capsules or modules may be powered by rechargeable batteries that may be recharged by an external battery charger using well-known inductive coil or antenna recharging means, and may contain electronic circuitry sufficient to permit telemetric communication with a programmer, to deliver electrical stimuli and/or sense electrical or other signals, and to store and execute instructions or data received from the programmer. Examples of methods and devices that may be adapted for use in the wireless devices and methods of the present invention include those described in U.S. Pat. No. 6,208,894 to Schulman et al. entitled "System of implantable devices for monitoring and/or affecting body parameters;" U.S. Pat. No. 5,876,425 to Schulman et al. entitled "Power control loop for implantable tissue stimulator;" U.S. Pat. No. 5,957,958 to Schulman et al. entitled "Implantable electrode arrays;" and U.S. patent application Ser. No. 09/030,106 filed Feb. 25, 1998 to Schulman et al. entitled "Battery-Powered Patient Implantable Device," now U.S. Pat. No. 6,185,452, all of which are hereby incorporated by reference herein, each in its respective entirety.

Figure 7B:
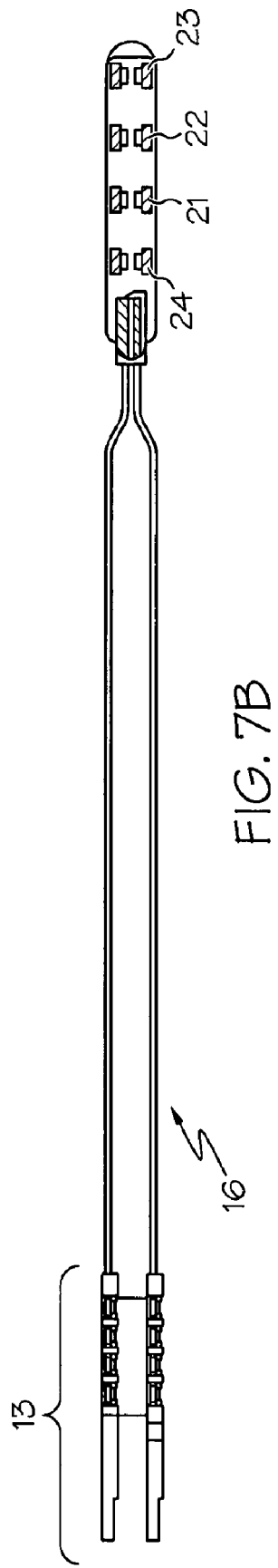
Figure 7C:
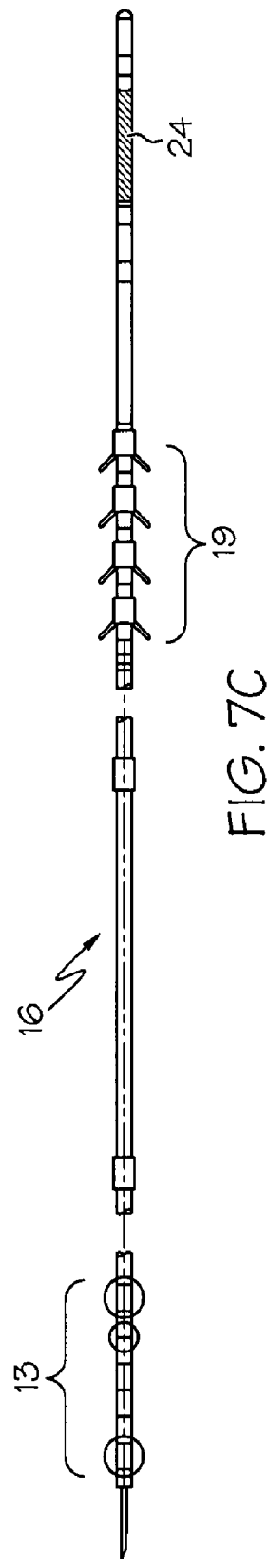
Figure 7D:
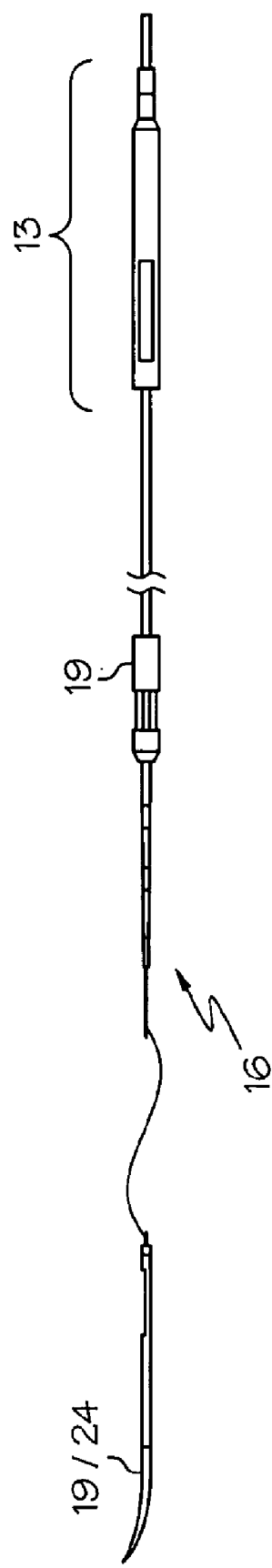
Figure 7E:
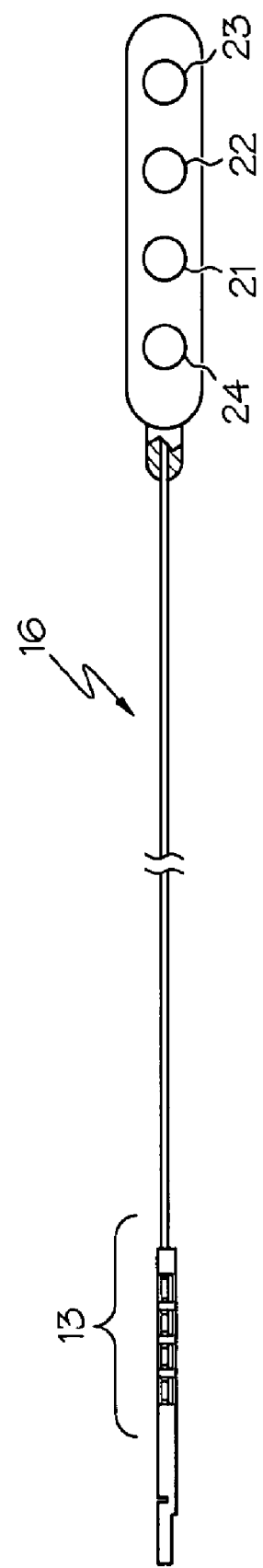
Figure 7F:
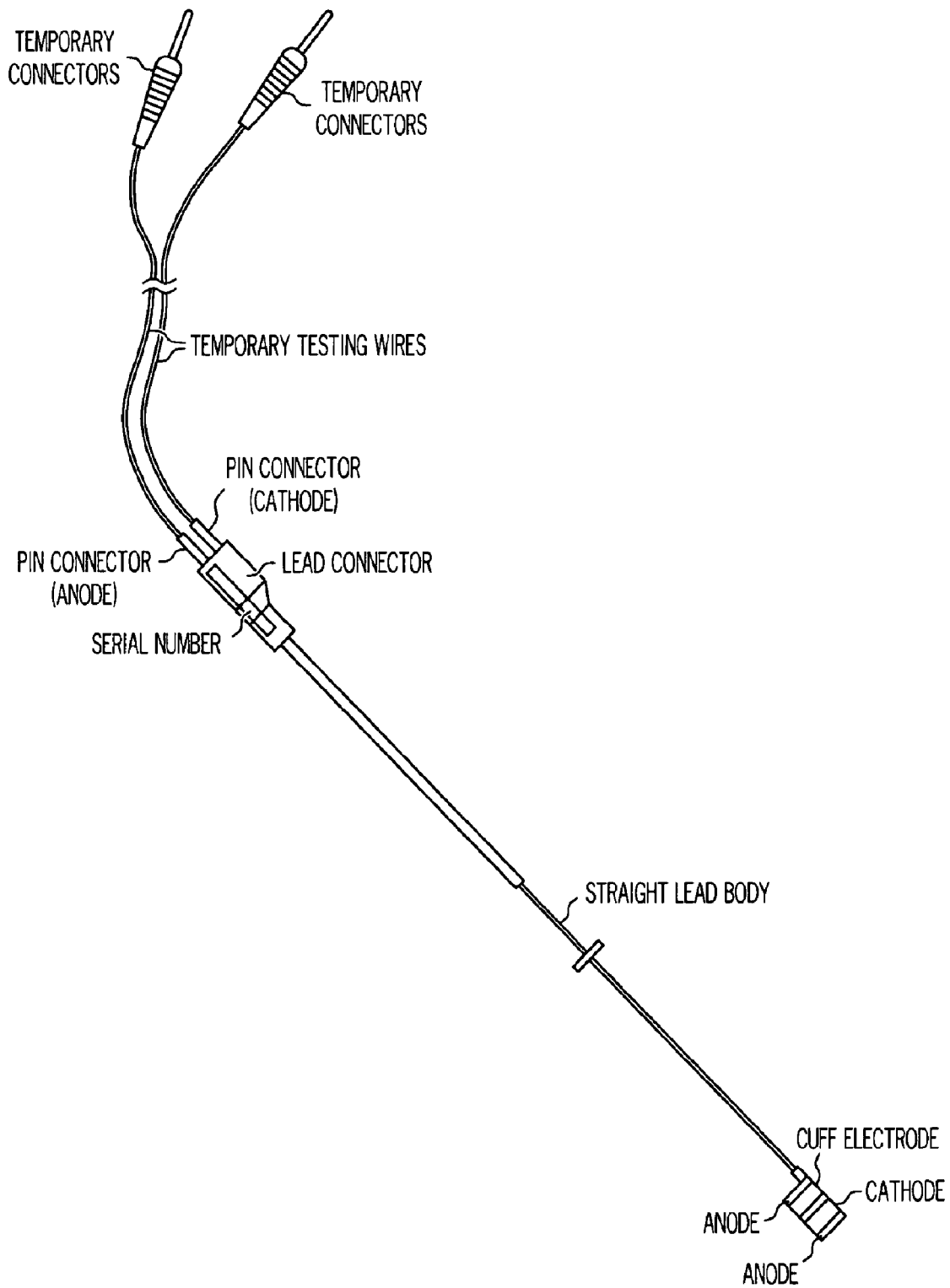

FIGS. 7B through 7F show various embodiments of the distal end of lead 16 of the present invention. In FIGS. 7B and 7E, lead 16 is a paddle lead where electrodes 21-24 are arranged along an outwardly facing planar surface. In FIG. 7C, lead 16 is a conventional quadrapolar lead having no pre-attached anchoring mechanism where electrodes 21-24 are cylindrical in shape and extend around the circumference of the lead body. In FIG. 7D, lead 16 is a quadrapolar lead having tined lead anchors. The tines may be formed from flexible or rigid biocompatible materials in accordance with the application at hand. Representative examples of some tined and other types of leads suitable, adaptable or modifiable for use in conjunction with the systems, methods and devices of the present invention include those disclosed in U.S. patent application Ser. No. 10/004,732 entitled "Implantable Medical Electrical Stimulation Lead Fixation Method and Apparatus", now U.S. Pat. No. 6,999,819, and Ser. No. 09/713,598 entitled "Minimally Invasive Apparatus for Implanting a Sacral Stimulation Lead", now U.S. Pat. No. 6,971,393, to Mamo et al., and those disclosed in U.S. Pat. No. 3,902,501 to Citron entitled "Endocardial Lead," U.S. Pat. No. 4,106,512 to Bisping entitled "Transvenously Implantable Lead," and U.S. Pat. No. 5,300,107 to Stokes entitled "Universal Tined Myocardial Pacing Lead." In FIG. 7D, lead 16 is a quadrapolar lead having a pre-attached suture anchor. In FIG. 7E, lead 16 comprises needle anchor/electrode 19/20 disposed at its distal end and suture anchor 19. FIG. 7F shows lead 16 as a tri-polar cuff electrode, where cuff/anchor 19 is wrapped around desired nerve or nerve portion 8 to thereby secure the distal end of lead 16 to the nerve and position electrodes 20-22 against or near nerve or nerve portion 8. The Medtronic Model No. 3995 cuff electrode lead is one example of a lead that may be adapted for use in the present invention, the Instructions for Use manual of which entitled "INTERSTIM Manual: Model 3995 Implantable bipolar peripheral nerve and spinal root stimulation lead" is hereby incorporated by reference herein in its entirety.

FIG. 7A illustrates one embodiment of an implantable stimulation system suitable for use in the present invention, where the system comprises pulse generator 101 and at least one associated medical electrical lead 16. Pulse generator 101 may be an implantable pulse generator such as a MEDTRONIC ITREL® 3 Model 7425 IPG that produces or generates an electrical stimulation signal adapted for the purposes of the present invention. IPG 101 may be surgically implanted such as in a subcutaneous pocket in the abdomen or positioned outside the patient. When positioned outside the patient, the pulse generator 101 may be attached to the patient. Pulse generator 101 may be programmed to modify parameters of the delivered electrical stimulation signal such as frequency, amplitude, duration, and pulse width in accordance with various embodiments of the present invention.

Any combination of stimulation signal parameters may be used. Preferably the combination of stimulation signal parameters is sufficient to stimulate a neuron. In an embodiment, the pulse width of a stimulation signal with which a neuron is stimulated may be within the range of about 10 μsec to about 600 μsec. In an embodiment, the pulse width is in the range of about 90 μsec to about 500 μsec. In another embodiment the pulse width is in the range of about 300 μsec to about 500 μsec. The frequency of a stimulation signal with which a neuron is stimulated may be, e.g., within the range of about 1 Hz to about 120 Hz. In an embodiment, the frequency is in the range of about 5 Hz to about 50 Hz. In another embodiment the frequency is in the range of about 5 Hz to about 20 Hz. The amplitude of a stimulation signal with which a neuron is stimulated may be, e.g., within the range of about 1 mA to about 20 mA. In an embodiment, the amplitude is in the range of about 5 mA to about 15 mA. In another embodiment the amplitude is in the range of about 8 mA to about 12 mA. It will be understood that the stimulation signal may include a voltage parameter rather than a current parameter. The voltage of a stimulation signal with which a neuron is stimulated may be, e.g., in the range of about 0.1 mV to about 30 V, about 1 V to about 20 V, or about 5 V to about 10 V. The duration of a stimulation signal with which a neuron is stimulated may be any duration to achieve a desired effect. Non-limiting examples of durations for which stimulation signals may be applied to a sympathetic neuron include the range between about 10 minutes and about 10 hours, the range between about 1 hour and about 6 hours, and the range between about 2 hours and about 4 hours.

Figure 9:
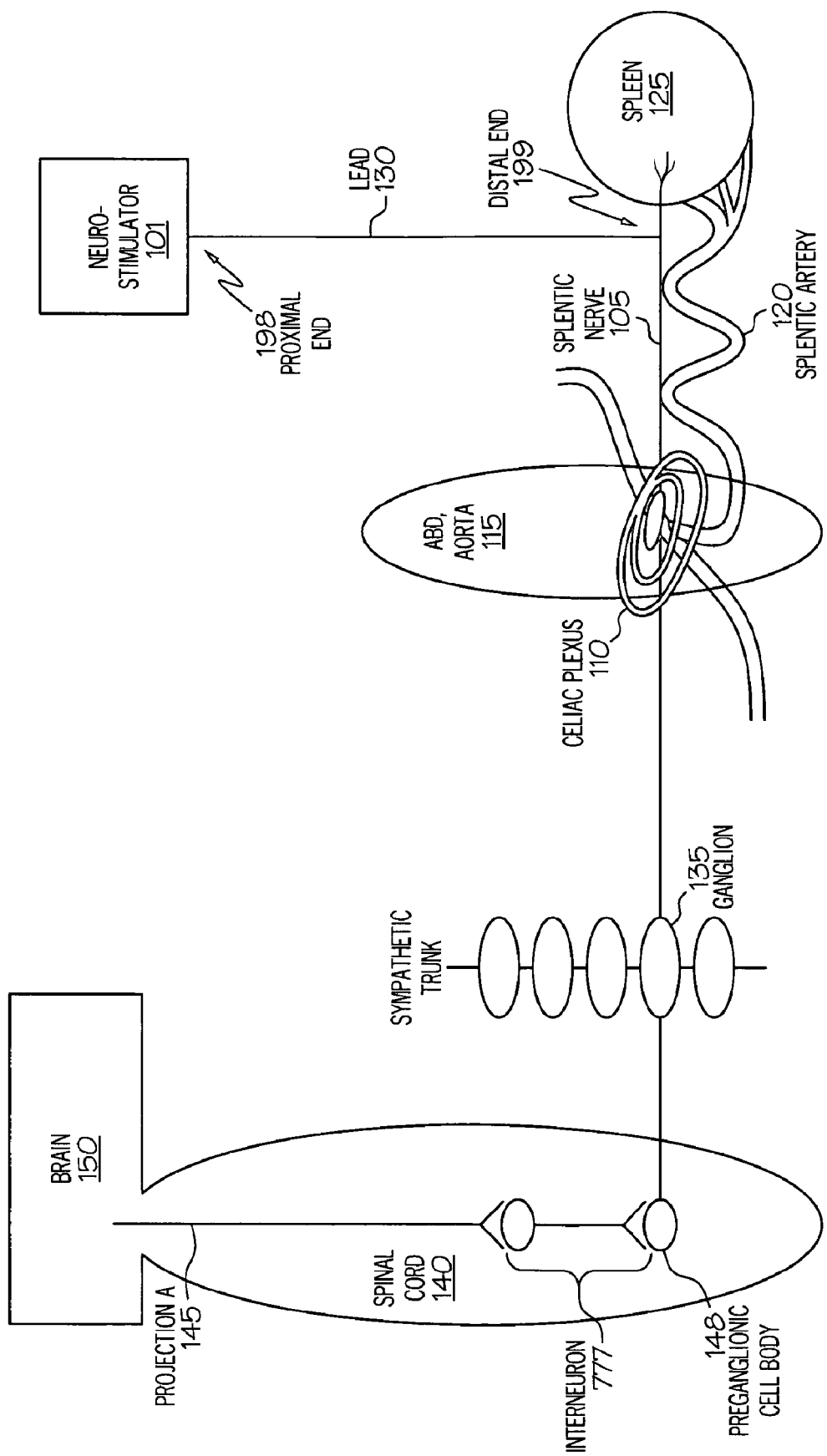
FIG. 9 is a diagrammatic illustration of a neurostimulatory device adapted to stimulate a splenic nerve according to an embodiment of the invention.

In an embodiment illustrated in FIG. 9, device 100 is a pulse generator 101 adapted to stimulate the splenic nerve 105 of a subject. While FIG. 9 shows a device 100 as a pulse generator 101, it will be understood that any device 100 capable of stimulating a sympathetic nervous system 10 of a subject when therapy delivery element 999 is positioned to deliver therapy to a target location 8 may be used in accordance with the invention. Such devices 100 include drug pumps with a catheter serving as therapy delivery element 999.

As shown in FIG. 9, the splenic nerve 105 runs as part of the greater splanchnic nerve 135 to the celiac plexus 110, which is found at the junction of the abdominal aorta 115 and the splenic artery 120, along the splenic artery 120 to innervate the spleen 125. A lead 16 is positioned to stimulate the splenic nerve 105. The lead 16 has a proximal end 198 coupled to the pulse generator and a distal end 199 adapted to stimulate the splenic nerve 105. The distal end 199 of the lead 16 may be positioned anywhere along the splenic nerve 105 or any region upstream of the splenic nerve 105, the stimulation of which would serve to stimulate the splenic nerve 105. Such upstream regions include the greater splanchnic nerve 135, the intermediolateral cell column of the lateral horn of the thoracolumbar spinal cord 140 at about T4-T10 where preganglionic cell body 148 of the splenic nerve resides, projections 145 from the CNS to preganglionic neurons at about T4-T10 of the thoracolumbar spinal column 140, preganglionic neurons and postganglionic neurons, as well as regions of the brain 150, including brainstem, midbrain such as the paraventricular nucleus of the hypothalamus, rostral ventrolateral medulla, ventromedial medulla, and caudal raphe nucleus, and the forebrain, which send projections a 145 to about T4-T10 of the thoracolumbar spinal cord 140, which contain cell bodies 148 of preganglionic neurons of the splenic nerve 105. The lead 16 may also be positioned to stimulate the spleen 125. The lead 16 may also be positioned to stimulate other tissue that is capable of transmitting a stimulatory signal to the splenic nerve.

In the embodiment illustrated in FIG. 9, the device 100 may take the form of a pulse generator 101, such as Test Stimulator Model 3625 manufactured by Medtronic, Inc. Lead 16 may take the form of any of the leads sold with the Model 3675, such as Model YY0050931R or other custom made leads.

The range of frequency with which the splenic nerve 105 undergoes an action potential may be varied by adjusting stimulation parameters of the pulse generator 101. Desired parameters will become evident upon treatment of a subject with stimulation therapy. Typically stimulation parameters of the pulse generator 101 will be adjusted such that the splenic nerve 105 will undergo an action potential at a frequency in the range of about 2 Hz to about 150 Hz, about 5 Hz to about 100 Hz, about 10 Hz to about 100 Hz, or about 10 Hz to about 50 Hz. In a specific embodiment to the splenic nerve of a subject is stimulated at 10 Hz with constant voltage of 10V and a pulse width of 450 µs.

2. Drug Pump

In an embodiment of the invention, device 100 is a drug pump and therapy delivery element 999 is a catheter. A drug pump system may include a catheter coupled to a pump. In an embodiment, the drug pump is an implantable drug pump.

Figure 10:
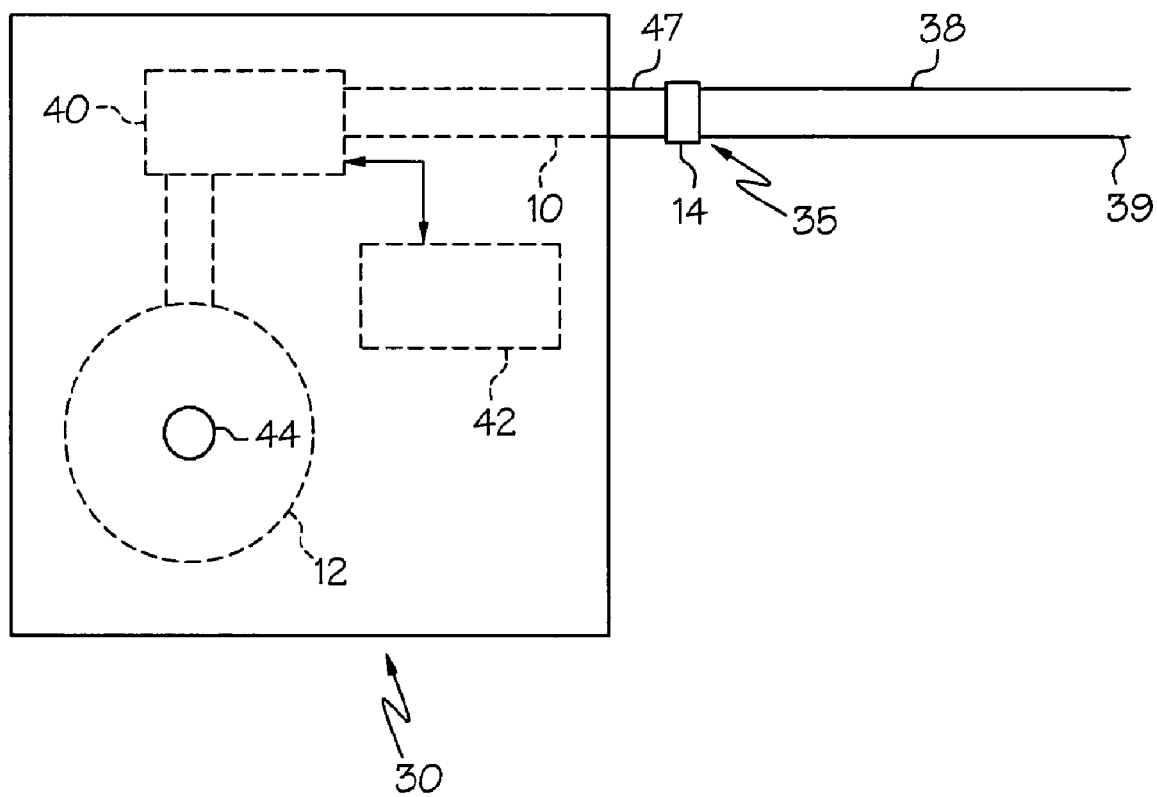
FIG. 10 is a drug pump system that may be used to stimulate a sympathetic nervous system according to an embodiment of the invention.

Referring to FIG. 10, a system according to an embodiment of the invention comprises a drug pump device 30. The drug pump device 30 comprises a pump 40 coupled to a reservoir 12 for housing a composition comprising a pharmacological agent. The system further comprises a catheter 38. The catheter 38 comprises a proximal portion 35 coupled to the pump 40 and a distal portion 39 adapted for infusing the composition to a target location 8. It will be recognized that the catheter 38 may have one or more drug delivery regions along the length of the catheter 38 and that a drug delivery region may or may not be at the distal end 39 of the catheter 38. The drug pump device 30 may be implantable or may be an external device. The drug pump device 30 may have a port 44 into which a hypodermic needle can be inserted to inject a quantity of therapeutic agent into reservoir 12. The drug pump device 30 may have a catheter port 47, to which the proximal portion 45 of catheter 38 may be coupled. The catheter port 47 may be coupled to pump 40 through an internal catheter 10. A connector 14 may be used to couple the catheter 38 to the catheter port 47 of the device 30. Drug pump device 30 may take the form of the device shown in U.S. Pat. No. 4,692,147 (Duggan), assigned to Medtronic, Inc., Minneapolis, Minn., commercially available as the Synchromed® infusion pump, which is incorporated by reference.

Drug pump device 30, such as Medtronic's SYNCHROMED pump system, may be operated to discharge a predetermined dosage of a pharmacological agent to a target location 8. The drug pump device 30 may contain a microprocessor 42 or similar device that can be programmed to control the amount of fluid delivery. The programming may be accomplished with an external programmer/control unit via telemetry. A controlled amount of fluid comprising one or more pharmacological agents may be delivered over a specified time period. With the use of a drug pump device 30, different dosage regimens may be programmed for a particular patient. Additionally, different therapeutic dosages can be programmed for different combinations of fluid comprising therapeutics. Those skilled in the art will recognize that a programmed drug pump device 30 allows for starting conservatively with lower doses and adjusting to a more aggressive dosing scheme, if warranted, based on safety and efficacy factors.

If it is desirable to administer more than one therapeutic agent, the composition within the reservoir 12 may contain a second, third, fourth, etc. therapeutic agent. Alternatively, the drug pump device 30 may have more than one reservoir 12 for housing additional compositions comprising a therapeutic agent. When the device 30 has more than one reservoir 12, the pump 40 may draw fluid from the one or more reservoirs 12 and deliver the drawn fluid to the catheter 38. The drug pump device 30 may contain a valve coupled to the pump 40 for selecting from which reservoir(s) 12 to draw fluid. Further, one or more catheters 38 may be coupled to the drug pump device 30. Each catheter 38 may be adapted for delivering a therapeutic agent from one or more reservoirs 12 of the device 30. A catheter 38 may have more than one lumen. Each lumen may be adapted to deliver a therapeutic agent from one or more reservoirs 12 of the pump 40. It will also be understood that more than one implantable device 30 may be used if it is desirable to deliver more than one therapeutic agent. Such drug pump devices, catheters, and systems include those described in, for example, copending application entitled IMPLANTABLE DRUG DELIVERY SYSTEMS AND METHODS, filed on Dec. 23, 2003, published as U.S. 2004/0220552, which application is hereby incorporated herein by reference.

Drug pump device 30 may be implanted below the skin of a patient. Preferably, the drug pump device 30 is implanted in a location where implantation interferes as little as practicable with patient activity. Drug pump device 30 may be implanted subcutaneously in any medically acceptable area of the human body, such as in an abdominal pocket.

According to an embodiment of the invention, distal end 39 of the catheter 38 is positioned to infuse a fluid into a target location 8. Catheter 38 may be positioned so that the distal tip 39 of catheter 38 is in proximity to target location 8.

A therapy delivery system may include an external drug pump device 30. The proximal end 45 of a catheter 38 may be coupled to the device and the distal end 39 of the catheter 38 may be positioned to deliver a therapeutic agent pumped from the external device 30 through the catheter 38 to a target location 8 within a subject. External delivery device 30 may be used as part of a drug trial system prior to use of an implantable pump system. Use of an external drug pump device 30 in such a manner provides an indication as to whether a patient will respond favorably to treatment prior to subjecting the patient to surgery associated with an implantable pump system. Any dose of therapeutic agent may be administered with an external therapy delivery device according to various embodiments of the invention. When used as a drug trial system, the dose of a therapeutic agent is typically started conservatively with lower doses and adjusted to higher doses until pain relief is noticed. It will also be recognized that single or multiple injections, without the use of a drug pump device 30, may also be used as to screen patients that are favorable candidates for an implantable therapy delivery device.

In an embodiment, a drug pump system is adapted to stimulate a sympathetic nervous system 10 or one or more neuron associated therewith. For example, a drug pump may deliver an agonist of a stimulatory neurotransmitter receptor (e.g., a glutamate receptor) or an antagonist of an inhibitory neurotransmitter receptor (e.g., a GABA receptor) to a region in close proximity to a neuron associated with a sympathetic neurotransmitter system. In addition, a cholinergic agonist may be administered to a region in close proximity to a ganglion of the sympathetic nervous system. In an embodiment, a sympathetic stimulatory agent is delivered in close proximity to ganglion associated with a sympathetic nerve that innervates a lymphoid tissue. Sympathetic stimulatory agents may be delivered anywhere along the sympathetic pathway, including at brain 150 areas such as the paraventricular nucleus of the hypothalamus, rostral ventrolateral medulla, ventromedial medulla, and caudal raphe nucleus, along projections 145a from the brain 150 to the preganglionic cell bodies 148, within the intermediolateral cell column of the lateral horn of the spinal cord 140 at T1-L2, along projections 146b that exit the spinal cord 140 through the ventral roots and go to sympathetic ganglia 135, at sympathetic ganglia 135, along a projection 146c of postganglionic neuron 148, and at or near an end organ 152.

In an embodiment, the drug pump system is adapted to mimic stimulation of a sympathetic nervous system. Agonists of receptors of neurotransmitters released from sympathetic neurons, such as norepinephrine, epinephrine, dopamine and substance P, may be delivered to an end organ to mimic stimulation of a sympathetic nervous system. Such agonists include epinephrine, norepinephrine, clonidine, methyl-Dopa, Guanabenz and other sympathomimetic agents, such as metaproteranol, terbutaline, fenoterol, albuterol, pirbuterol and salmeterol, and the like. Preferably, agonists of receptors of neurotransmitters released from sympathetic neurons are administered in close proximity to a lymphoid tissue or organ. Similarly, an alpha adrenergic antagonist, including terazozin, doxazosin, tamulosin, parazosin, and the like, may be administered.

When a drug pump device 30 is employed, the amount of a pharmacological agent may be closely controlled. For example, an agent may be released in a pulsating manner or may be continuously infused.

Modification of Stimulation Parameters

Figure 11:
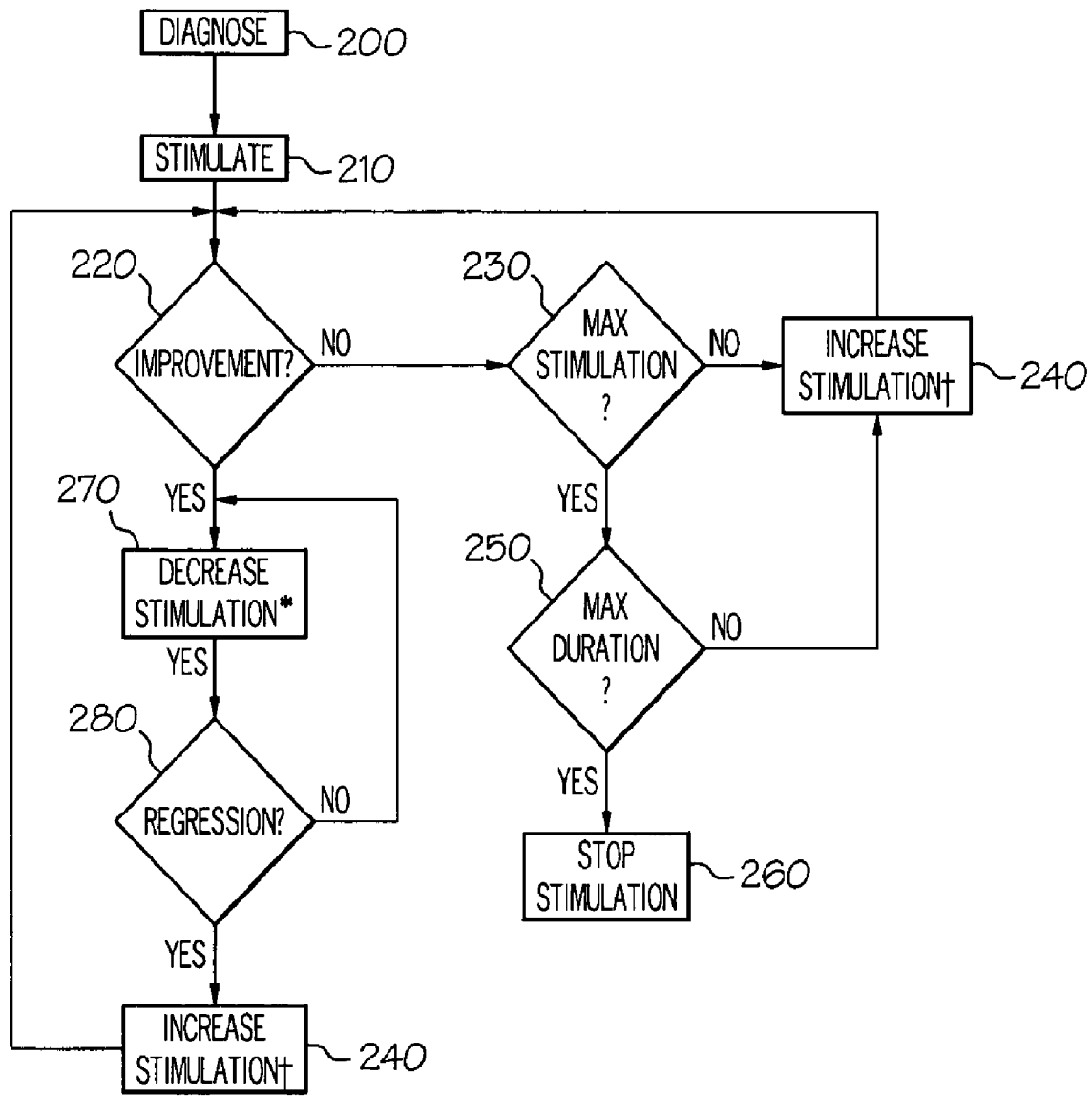
FIG. 11 is a flow chart illustrating how stimulation of a sympathetic nervous system may be modified according to an embodiment of the invention.

FIG. 11 illustrates an embodiment of the invention where the extent of stimulation of one or more sympathetic neuron may be varied during the course of stimulation therapy. At step 200, a subject is diagnosed and it is determined whether the subject has an immune response for which attenuation may be beneficial. Subjects for which attenuation of an immune response may be beneficial include subjects experiencing a deleterious characteristic, disorder, or disease associated with an immune response. In an embodiment, the subject is suffering from a deleterious characteristic, disorder, or disease associated with an inflammatory immune response. The diagnosis 200 may be accompanied by an assessment of one or more of levels of immune mediators, measurements of objective symptoms related to the deleterious characteristic, disorder, and/or disease state of an immune response, and the subject's perception as to the extent of the symptoms. After a subject is diagnosed 200 as having an immune response for which attenuation may be beneficial, the stimulation of the subject's sympathetic nervous system is initiated 210. An initial set of stimulation parameters may be set based on the degree of the patient's deleterious characteristic, disorder, or disease associated with an immune response. The initial stimulation parameters may also vary depending on the one or more neurons to be initially stimulated 210. Such parameters will become evident in practice by the skilled clinician. After initial stimulation 210, a determination may be made as to whether the stimulation 210 resulted in an improvement 220 in the subject's condition. Improvement 220 can be assessed by one or more changes in levels of immune mediators, objective changes in symptoms related to the deleterious characteristic, disorder, and/or disease state of an immune response, changes in the subject's perception as to the extent of the symptoms, and the like. One or more criterion for determining an improvement 220 can be determined by a skilled clinician in practice. Algorithms for determining whether overall criteria are met may be employed and may be useful where more than one criterion is used to determine whether improvement 220 has occurred. If criteria for improvement 220 are not met, a determination of whether maximal stimulation 230 parameters have been met may be performed. Maximal stimulation 230 parameters may be determined prior to initiation of stimulation 210 therapy or may be determined during therapy as conditions warrant. If maximum stimulation 230 parameters for stimulation of the subject's sympathetic nervous system have been met, a determination may be made as to whether the subject's sympathetic nervous system has been stimulated at maximal stimulation 230 for a maximal duration 250. The maximal duration 250 of maximal stimulation 230 may be determined prior to initiation of stimulation 210 therapy or may be determined during therapy. If the subject's sympathetic nervous system has been maximally stimulated 230 for the maximal duration 250, stimulation may be stopped 260. If the maximal duration 250 of maximal stimulation 230 has not been reached or if maximal stimulation 230 parameters have not been met, the stimulation signal may be increased 240. After the stimulation signal is increased 240, a determination may be made as to whether the increased stimulation 240 resulted in an improvement 220 in the subject's condition. If no improvement 220 is detected, a determination may again be made as to whether maximum stimulation 230 parameters have been met and as to whether maximal duration 250 at maximal stimulation 230 has been achieved. If maximal stimulation 230 and maximal duration 250 parameters have not been met, the stimulation may again be increased 240. If the parameters have been met, stimulation may be stopped 260.

If, at any time after stimulation therapy is initiated 210, an improvement 220 is detected, the stimulation signal may be decreased 270. The extent to which the stimulation signal may be decreased 270 may be determined prior to initiation of stimulation 210 therapy or may be determined during therapy as conditions warrant. For example, a marked improvement 220 may warrant a greater decrease 270 in stimulation than a slight improvement 220. After decreasing stimulation 270, a determination may be made as to whether the decreased stimulation 270 resulted in a regression 280 in the subject's condition. Regression 280 can be assessed by one or more of changes in levels of immune mediators, objective changes in symptoms related to the deleterious characteristic, disorder, and/or disease state of an immune response, changes in the subject's perception as to the extent of the symptoms, and the like. One or more criterion for determining a regression 280 can be determined by a skilled clinician in practice. Algorithms for determining whether overall criteria are met may be employed, and may be useful where more than one criterion is used to determine whether regression 280 has occurred. If criteria for regression 280 have not been met, the stimulation may be further decreased 270. The subject may then again be assessed for regression 280. If regression is not detected, the stimulation may be further decreased 270. Eventually, stimulation may be decreased 270 to a point where stimulation is ceased. If, at any point after decreasing stimulation 270, a regression 280 is detected, stimulation may be increased 240. A determination may then be made as to whether an improvement 220 resulted from the increased stimulation 240 to determine whether to a) further increase stimulation 240, b) stop stimulation 260 due to maximal stimulation 230 for maximal duration 250, or c) decrease stimulation 270.

Prior to initiation of stimulation 210 therapy, the subject may be diagnosed 200 as having an immune response for which stimulation of the subject's sympathetic nervous system may be beneficial. Diagnosis 200 may include determining whether the patient has a symptom of a deleterious characteristic, disease, and/or disorder of an immune response, determining the level of a mediator of an immune response in the subject, determining the level of a mediator of an anti-immune response in the subject, and the like. If a subject has a symptom of a deleterious characteristic, disease, and/or disorder of an immune response, the symptom may be quantified. A symptom may be quantified either objectively or subjectively, through, e.g., the subject's perception of improvement. Attenuation of an immune response 20, used in FIG. 6 as "improvement" 220, may be detected, relative to the diagnosis 210, by measuring a reduction in a quantified symptom of a deleterious characteristic, disease, and/or disorder of an immune response, a reduction in the level of a mediator of an immune response, an increase in the level of an anti-immune response, and the like, or a combination thereof. As used herein, "attenuating an immune response" means to reduce the ability of a subject to produce an immune response, reduce the ability of a subject to produce mediators of an immune response, increase the ability of a subject to produce an anti-immune response, and/or increase the ability of a subject to produce mediators of an anti-immune response. Any measurable mediator or symptom associated with an immune response or anti-immune response may be used to diagnose 210 a subject or to determine whether a subject has undergone an improvement 220 or a regression 280. As used herein, "regression" 280 means an unfavorable or undesirable change in a deleterious characteristic or symptom of a disorder or disease state, which change follows a prior improvement in a deleterious characteristic or symptom of a disorder or disease state. For example, if the level of a mediator of an immune response in a subject were first found to decrease, thus marking an improvement 220, and then found to increase, the latter increase would be considered a regression 280.

One or more condition 310 of a subject associated with an immune response or with stimulation of a neuron may be assessed to determine a health state of the subject. Improvements 220 and regressions 280 of the health state of the patient may be assessed based on changes in the one or more conditions 310.

Sensor

Figure 12:
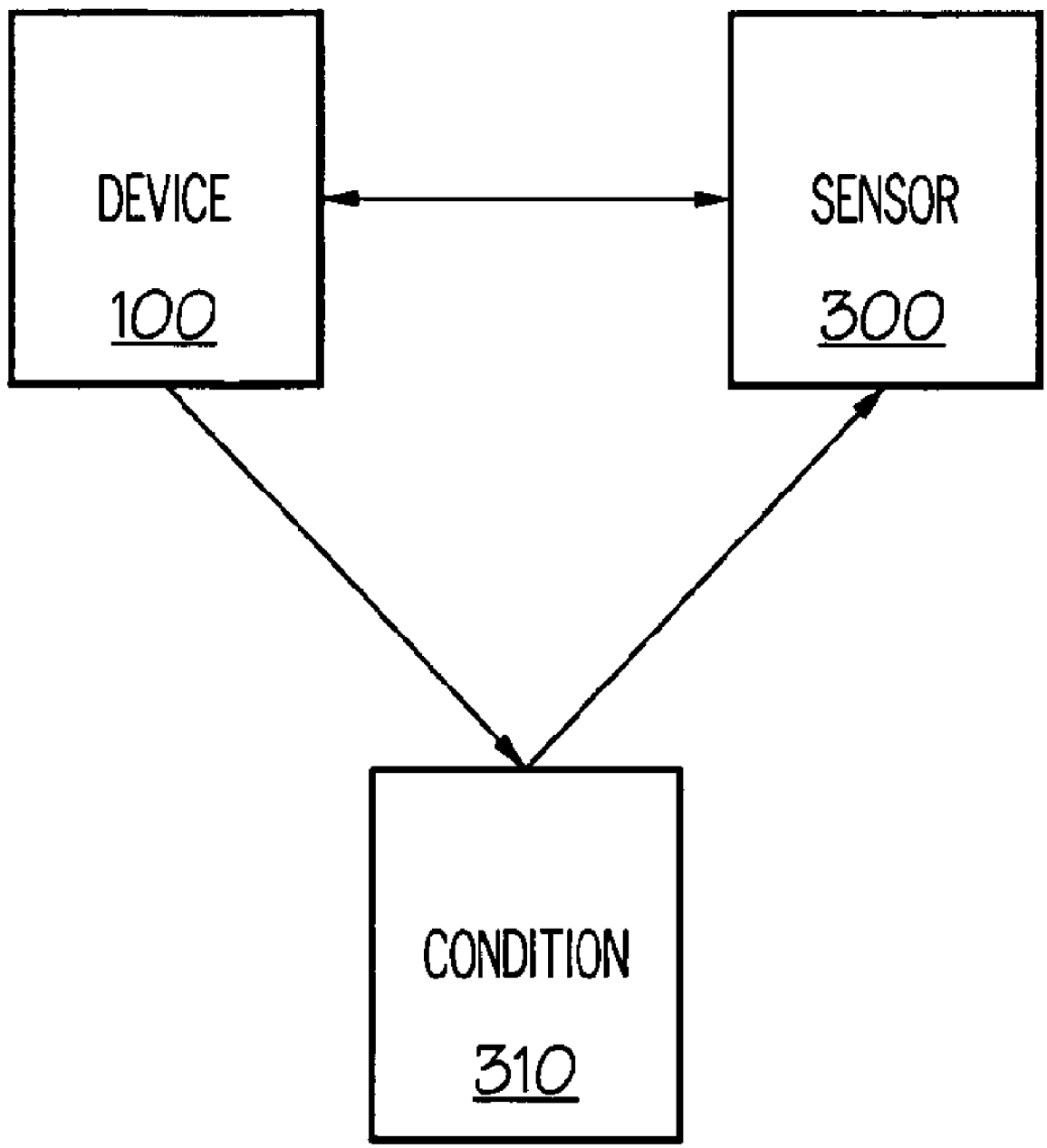
FIG. 12 is diagrammatic illustration of an embodiment of the invention including a sensor.

FIG. 12 illustrates an embodiment of the invention where a sensor 300 can detect a condition 310. A sensor 300 may detect a condition 310 prior to initiation of therapy or at any time during therapy. The sensor 300 may be coupled to a device 100, which can generate or modify a condition 310. The sensor 300 may modify parameters of the device 100 to change the ability of the device 100 to generate or modify the condition 310. The device 100 may stimulate a sympathetic neuron to attenuate an immune response 20. The condition 310 generated or modified by the device 100 can thus be a condition 310 associated with stimulation of a neuron or a condition 310 associated with attenuation of an immune response 20. Any condition 310 associated with stimulation of a sympathetic nervous system 10 or associated with attenuation of an immune response 20 may be detected by sensor 300. A condition 310 associated with attenuation of an immune response 20 can be, for example, a deleterious characteristic or symptom associated with a disorder or disease associated with an immune response 20. A condition 310 associated with stimulation of a sympathetic neuron can be, for example, membrane potential of a neuron, frequency with which the stimulated neuron undergoes an action potential, or level or amount of a sympathetic neurotransmitter 154 released from the neuron or present in the subject.

Figure 13A:
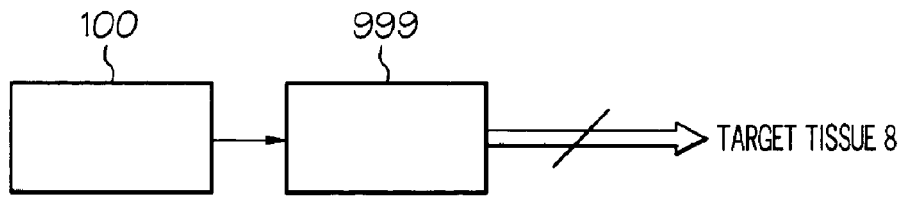
FIG. 13A-13C are block diagrams of (A) one embodiment of an open-loop stimulation system of the present invention; (B) one closed-loop embodiment of a stimulation system of the present invention; and (C) another embodiment of a closed loop electric stimulation system of the present invention.
Figure 13B:
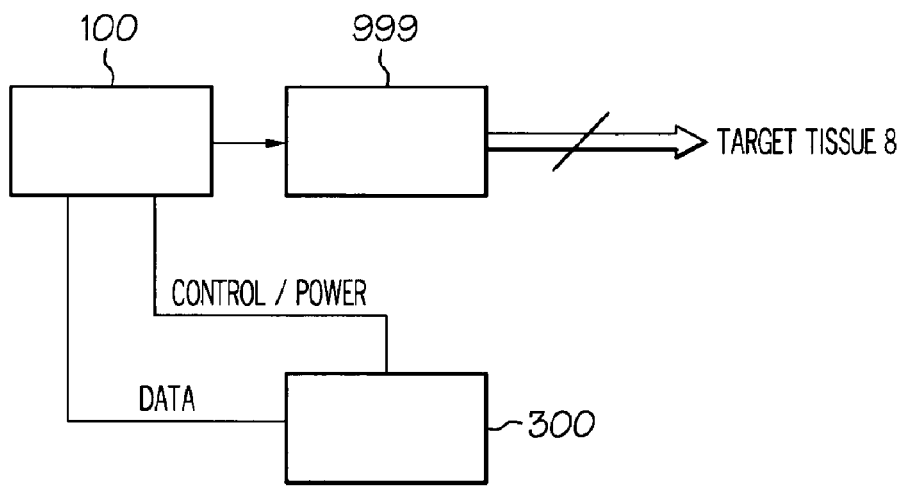
Figure 13C:
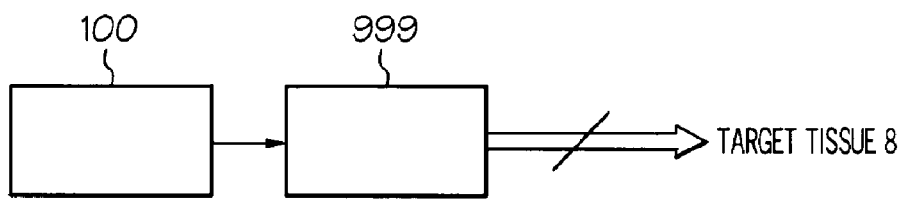
Figure 13C:
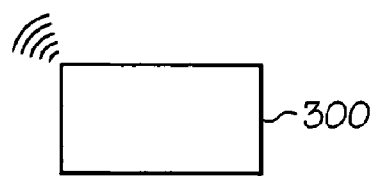

FIG. 13A shows a block diagram of one embodiment of an open-loop therapy delivery system of the present invention. The therapy delivery system comprises a device 100 and a therapy delivery element 999 adapted to deliver a stimulation signal to a target tissue location 8. The device 100 may be, e.g., a pulse generator or a drug pump, which may be external to or implantable within a subject. FIG. 13B shows a block diagram of a closed-loop therapy delivery system according to an embodiment of the invention. FIG. 13C shows a block diagram of yet another embodiment of a closed loop therapy delivery system according to an embodiment of the present invention having a wireless connection between sensor 300 and device 100.

In a closed-loop feedback control embodiment of the present invention, sensor 300 and sensing and computing circuitry in device 100 cooperate to detect when a sensed signal has fallen below or risen above a predetermined threshold, as the case may be. Once the sensed signal has remained above or below the predetermined threshold for a predetermined period of time, therapy delivery circuitry in device 100 may be disabled. Such therapy delivery circuitry in device 100 may be subsequently enabled or activated when the sensed signal has once again risen above or fallen below the same or a different predetermined threshold. Similarly, therapy delivery circuitry in device 100 may be enabled when the sensed signal has remained above or below the predetermined threshold for a predetermined period of time, and such circuitry may subsequently be disabled or inactivated when the sensed signal has once again risen above or fallen below the same or a different predetermined threshold.

Sensor 300 may detect biochemical parameters, physiological parameters, and combinations thereof. Biological parameters include pH, a chemical, an ion, a biological molecule, a gas, spectral indicators thereof, and combinations thereof. Physiological parameters such as body temperature, heart rate, blood pressure, cardiac output, electrical activity of a neuron, and the like, or combinations thereof.

Some examples of sensor technology that may be adapted for use in some embodiments of the present invention include those disclosed in the following U.S. patents:

U.S. Pat. No. 5,640,764 for "Method of forming a tubular feed-through hermetic seal for an implantable medical device;"
U.S. Pat. No. 5,660,163 for "Glucose sensor assembly;"
U.S. Pat. No. 5,750,926 for "Hermetically sealed electrical feedthrough for use with implantable electronic devices;"
U.S. Pat. No. 5,791,344 for "Patient monitoring system;"
U.S. Pat. No. 5,917,346 for "Low power current to frequency converter circuit for use in implantable sensors;"
U.S. Pat. No. 5,957,958 for "Implantable electrode arrays;"
U.S. Pat. No. 5,999,848 for "Daisy chainable sensors and stimulators for implantation in living tissue;"
U.S. Pat. No. 6,043,437 for "Alumina insulation for coating implantable components and other microminiature devices;"
U.S. Pat. No. 6,088,608 for "Electrochemical sensor and integrity tests therefor;"
U.S. Pat. No. 6,259,937 for "Implantable substrate sensor."

Each of the foregoing patents is incorporated by reference herein, each in its respective entirety.

Sensor 300 may be any means capable of detecting a condition 310 associated with simulation of a sympathetic neuron or associated with attenuation of an immune response 20. Non limiting examples of suitable sensors 300 include a test kit; a chemical or biological assay; an electrical probe; thermodilution system; pressure sensor; microchip and the like.

In an embodiment, sensor 300 may include a probe capable of detecting electrical activity of a neuron. Such electrical activity includes the membrane potential of a neuron and the frequency with which a neuron undergoes an action potential. Probes capable of measuring such electrical activity include intracellular probes, extracellular probes, and patch clamps. Specific commercially available probes of this nature include Bio Amp/ Stimulation systems (Power Lab AD instruments). In addition, the probe may detect electrical activity of a region of tissue comprising a neuron.

In an embodiment, sensor 300 may detect the amount of neurotransmitter 154 released from a stimulated sympathetic nerve. The amount of neurotransmitter 154 released may be measured by determining the amount or level of the neurotransmitter 154 or its metabolites at the nerve terminal, within the region of the nerve terminal, systemically, at the site of desired neurotransmitter 154 action, and/or at any site that is apparent to a clinician practicing one or more embodiments of the invention. Means for detecting the level of neurotransmitter 154 include an electrode with an ion selective coating applied which is capable of directly transducing the amount of a particular transmitter substance or its metabolic by-products. An example of this type of transducer is described in the paper "Multichannel semiconductor-based electrodes for in vivo electrochemical and electrophysiological studies in rat CNS" by Craig G. van Home, Spencer Bement, Barry J. Hoffer, and Greg A. Gerhardt, published in Neuroscience Letters, 120 (1990) 249-252.

In an embodiment, the level of norepinephrine is detected by the sensor 300. Any method and sensor capable of detecting norepinephrine may be employed. For example, norepinephrine may be detected by microdialysis, chromatography and microchip. Norepinephrine is typically rapidly degraded after release by enzymes such as 3-methoxy-4-hydroxyphenylethyleneglycol (MHPG) and 3,4-dihydroxyphenylethylene-glycol (DHPG). Thus, metabolites of norepinephrine such as MHPG and DHPG may be detected by sensor 300.

In an embodiment, sensor 300 may detect a deleterious characteristic or symptom associated with a disorder or disease associated with an immune response. For example, the sensor 300 may detect the level of cytokine, body temperature, white blood cell count, subjective severity, and the like.

Sensor 300 may be external to the subject or may be implantable. Examples of implantable sensors capable of detecting biochemical or physiological parameters include recording electrodes for detecting the electrical activity of a neuron or tissue regions comprising neurons, transducers capable of detecting amounts of a chemical including a neurotransmitter or its metabolites, cytokine, adhesion molecule, neurotrophic factor and other immune markers. These parameters are related to attenuation of an immune response in that they are all involved in the inflammatory cascade.

Figure 14:
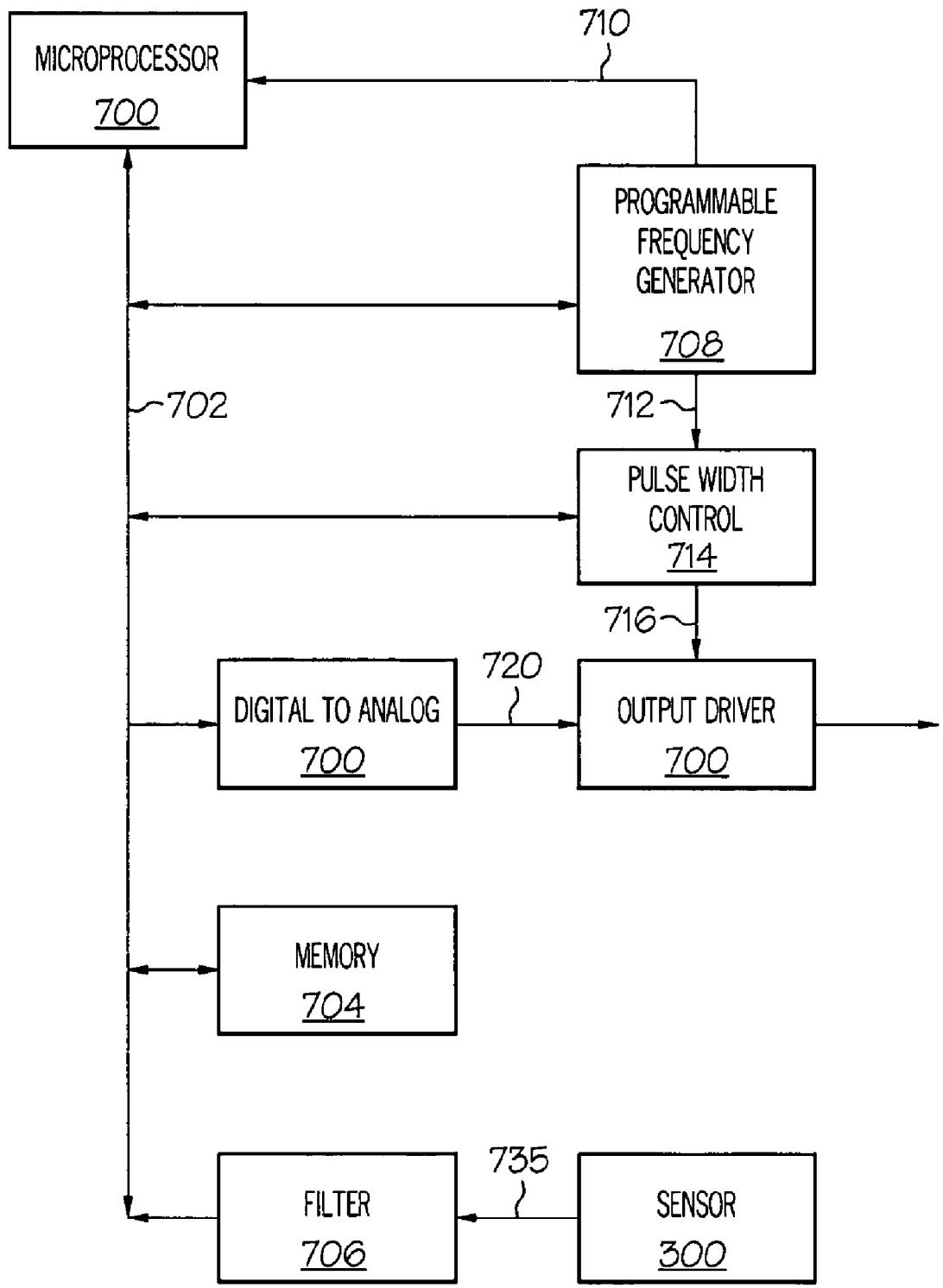
FIG. 14 is a schematic block diagram of a microprocessor and related circuitry for utilizing a sensor to control stimulation administration to a sympathetic nervous system according to an embodiment of the invention.

In an embodiment, sensor 300 is coupled to device 100 to modify parameters of the device 100 such that the device 100 increases stimulation 240 or decreases stimulation 270 of a sympathetic neuron. FIG. 14 reveals an embodiment where sensor 300 is coupled to filter 706 of device 100 through coupler 735. Sensor 300 may be coupled to device 100 through any means capable of transmitting information from the sensor 300 to the device 100. For example, the output of sensor 300 may be coupled by cable, comprising conductors, to an analog to digital converter within device 100. Alternatively, the output of sensor 300 may communicate with the device 100 through a telemetry downlink. The output from sensor 300 can be filtered by an appropriate electronic filter 706 in order to provide a control signal for device 100.

In the embodiment shown in FIG. 14, device 100 is a pulse generator 101. It will be recognized that other devices 100, such as a drug pump, etc., may be connected to a sensor. Referring to FIG. 8, the output of the filter 706 may be connected to a microprocessor 700 through a peripheral bus 702 including address, data and control lines. Microprocessor 700 processes the sensor data in different ways depending on the type of transducer in use. When the signal on sensor 300 exceeds or is below a level programmed by a clinician and stored in a memory 704, stimulation applied through an output driver 724 will be appropriately increased 240 or decreased 270. The stimulus pulse frequency of the pulse generator 101 is controlled by programming a value to a programmable frequency generator 708 using bus 702. The programmable frequency generator provides an interrupt signal to microprocessor 700 through an interrupt line 710 when each stimulus pulse is to be generated. The frequency generator implemented may be model CDP1878 sold by Harris Corporation. The amplitude for each stimulus pulse may be programmed to a digital to analog converter 718 using bus 702. The analog output may be conveyed through a conductor 720 to an output driver circuit 724 to control stimulus amplitude.

Microprocessor 700 may also program a pulse width control module 714 using bus 702. The pulse width control provides an enabling pulse of duration equal to the pulse width via a conductor 716. Pulses with the selected characteristics are then delivered from pulse generator 101 through lead 16 to stimulate a sympathetic nervous system 10 or one or more neuron associated therewith.

System

Figure 15:
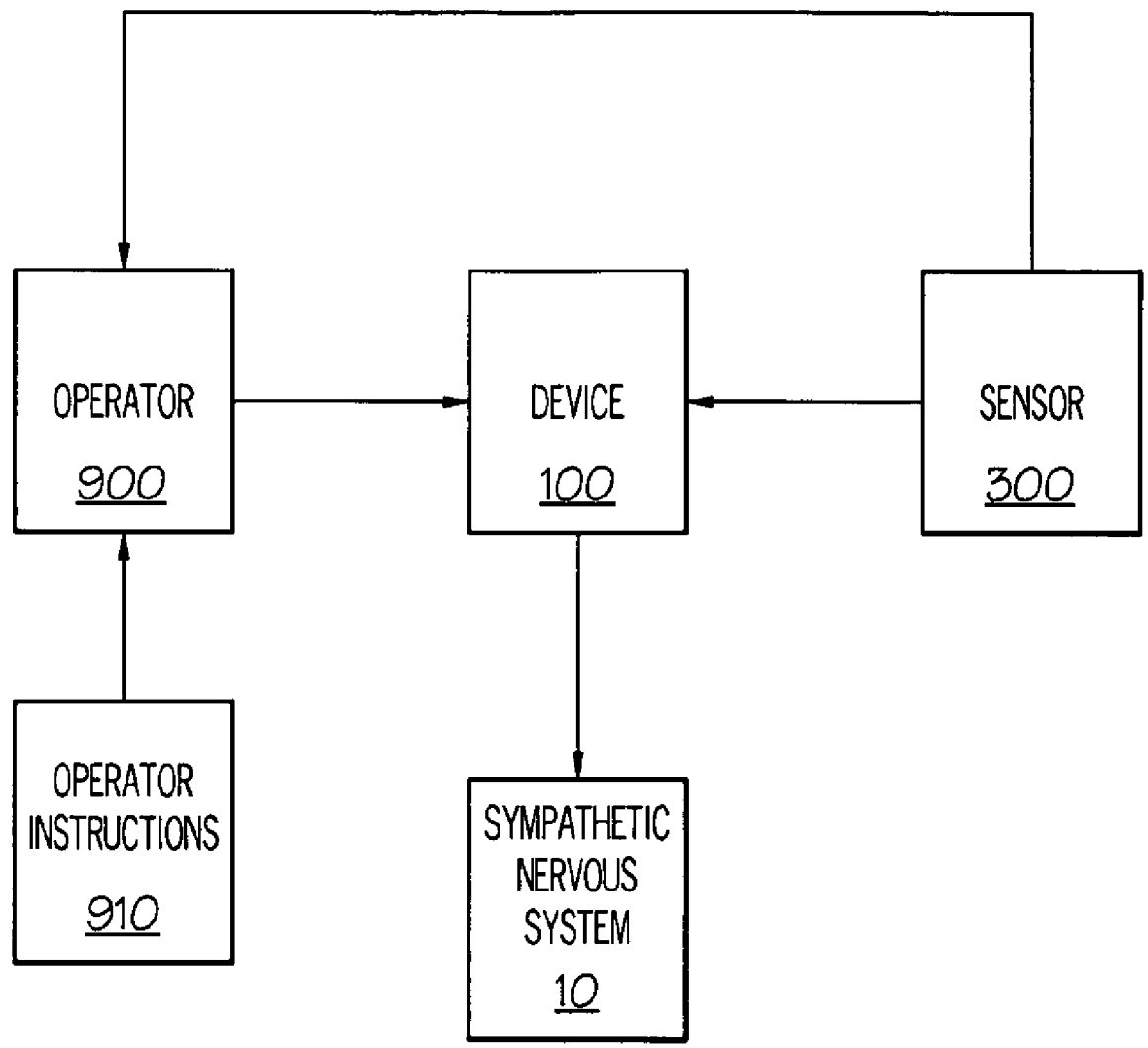
FIG. 15 is a diagrammatic illustration of a system according to an embodiment of the invention.

An embodiment of the invention provides a system for attenuating an inflammatory immune response. As shown in FIG. 15, the system may include a device 100 capable of stimulating a sympathetic nervous system 10 of a subject. An operator 900 may provide the device 100, via device memory 704, with parameters for carrying out stimulation of the sympathetic nervous system 10 or one or more neurons associated therewith. The operator 900 may be a subject or may be a health care professional or other caregiver. The system may contain instructions 910 for the operator regarding how to operate the device 100 to stimulate the sympathetic nervous system 10. The instructions 910 may simply indicate that the system is capable of attenuating an immune response by stimulating a sympathetic nervous system 10 or one or more neurons thereof. The system may also include one or more sensor 300 for detecting a condition 310, which may be generated or modified by the device 100. In some embodiments, the sensor 300 may directly modify stimulation parameters of the device 100 based on one or more detected condition 310. In other embodiments, the sensor 300 may serve to notify an operator 900 of a detected condition 310. The operator 900 may modify stimulation parameters of the device 100 based on information received from the sensor 300. In some embodiments, the sensor 300 may be the operator 900.

The invention may also be embodied as a computer-readable medium that includes instructions to cause a processor to perform any of the methods described herein. These and other embodiments are within the scope of the following claims.

All patents, patent applications, technical papers, and publications cited herein are hereby incorporated by reference herein, each in its respective entirety. As those of ordinary skill in the art will readily appreciate upon reading the description herein, at least some of the devices and methods disclosed in the patents and publications cited herein may be modified advantageously in accordance with the teachings of the present invention.

EXAMPLE

The following example is provided to illustrate specific embodiments of the invention only, and should not be construed as limiting the scope of the invention.

Methods

A porcine model of endotoxic shock was established previously for use in the following procedure. Here, the porcine model was validated and the effects of systemic LPS administration (decreased WBC count, increased pro-inflammatory cytokines, etc.) were demonstrated to be consistent with sepsis models of other species. The dose of endotoxin administered is generally lethal within 8 hrs if no attempt at recovery is made. Pigs (50-80 kg) were housed at 22° C. on a 12 hr light/dark cycle. The animals were cared for and housed at Physiological Research Laboratories (Coon Rapids, Minn.) in individual runs that meet the weight-space specifications recommended in The Guide for the Care and Use of Laboratory Animals. The protocol was in compliance with the Animal Welfare Act of 1966 (P.L. 89-544), and all amendments. Experiments were performed under the protocols approved by the Institutional Animal Care and Use Committee.

Verapamil (SR) (360 mg, SID) was administered the afternoon of the day prior to surgery and again the morning of surgery. The morning of surgery sedation was induced with Acepromazine 1.1 mg/kg IM given approximately ½ hr prior to anesthesia induction, followed by Xylazine 1 mg/kg and Ketamine 11 mg/kg given together IM, masked down on Isoflurane to an appropriate plane of anesthesia, intubated and maintained on Isoflurane.

Figure 16A:
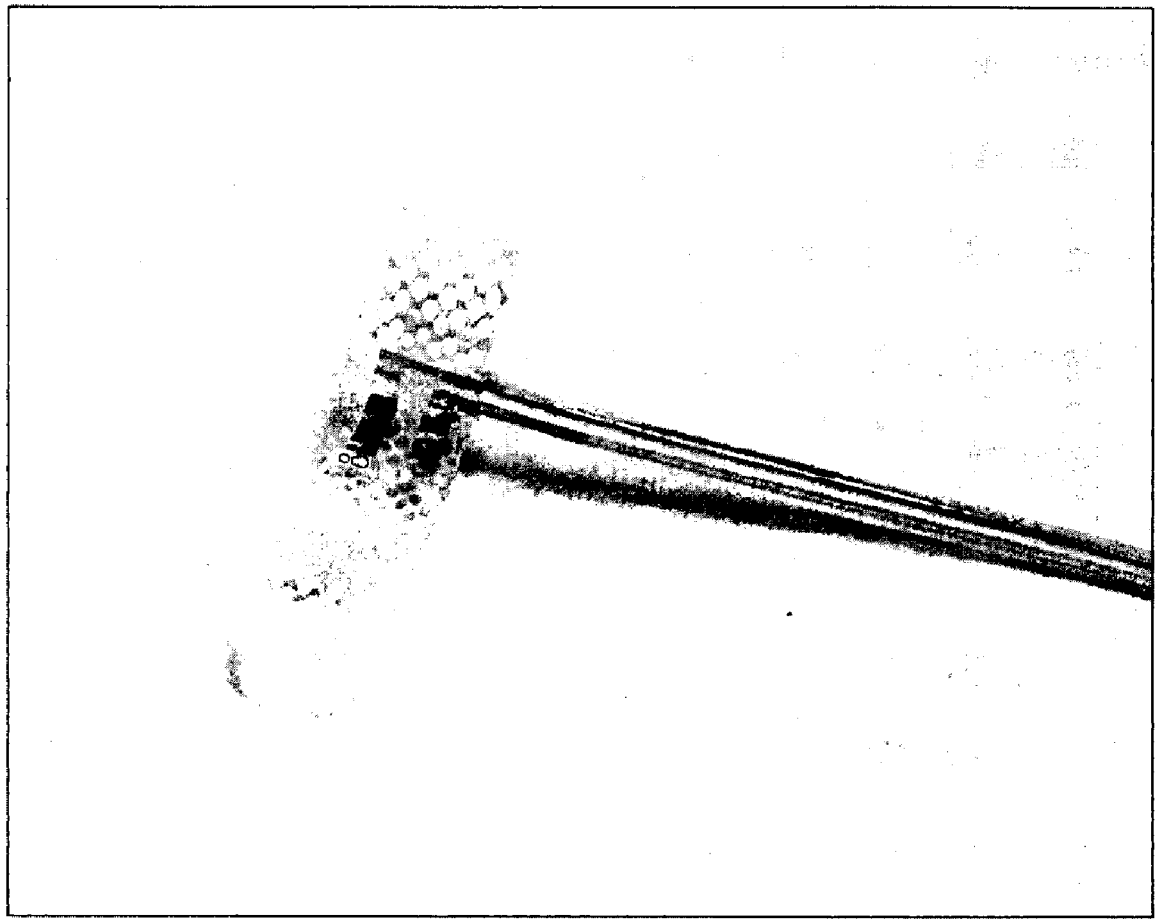
FIG. 16 is a photograph of the cuff electrode used to stimulate the splenic nerve in one embodiment.
Figure 16B:
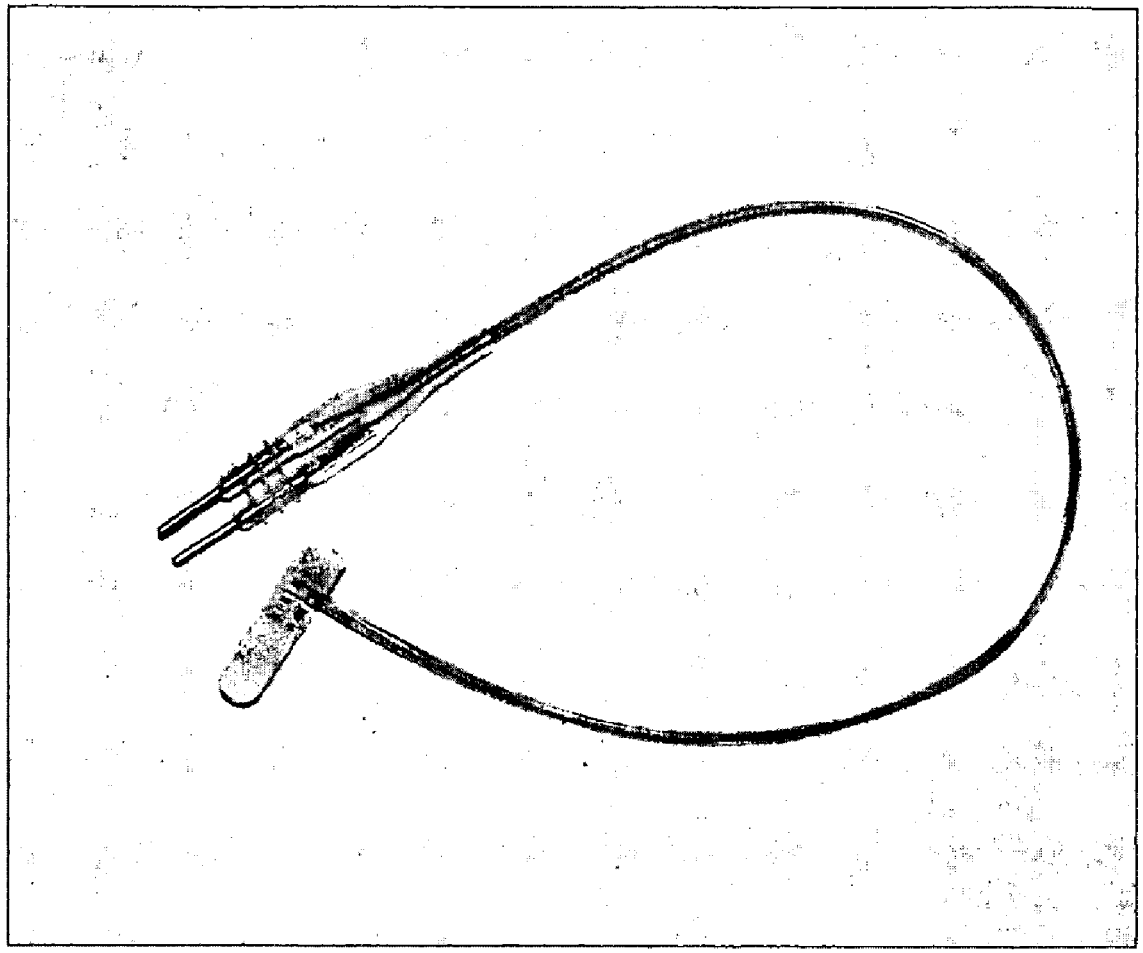
Figure 17A:
FIG. 17 is a photograph showing A) Simple surgical approach-lateral flank incision, cuff electrode was attached in the vicinity of scissor tips. B) Tissue reflected upon necropsy to show electrode placement. C) Higher magnification of B, to demonstrate the branches of nerve and artery within cuff electrode. D) Histology of tissue under the cuff electrode after stimulation of various frequencies (1-120 Hz)
Figure 17B:
Figure 17C:
Figure 17D:
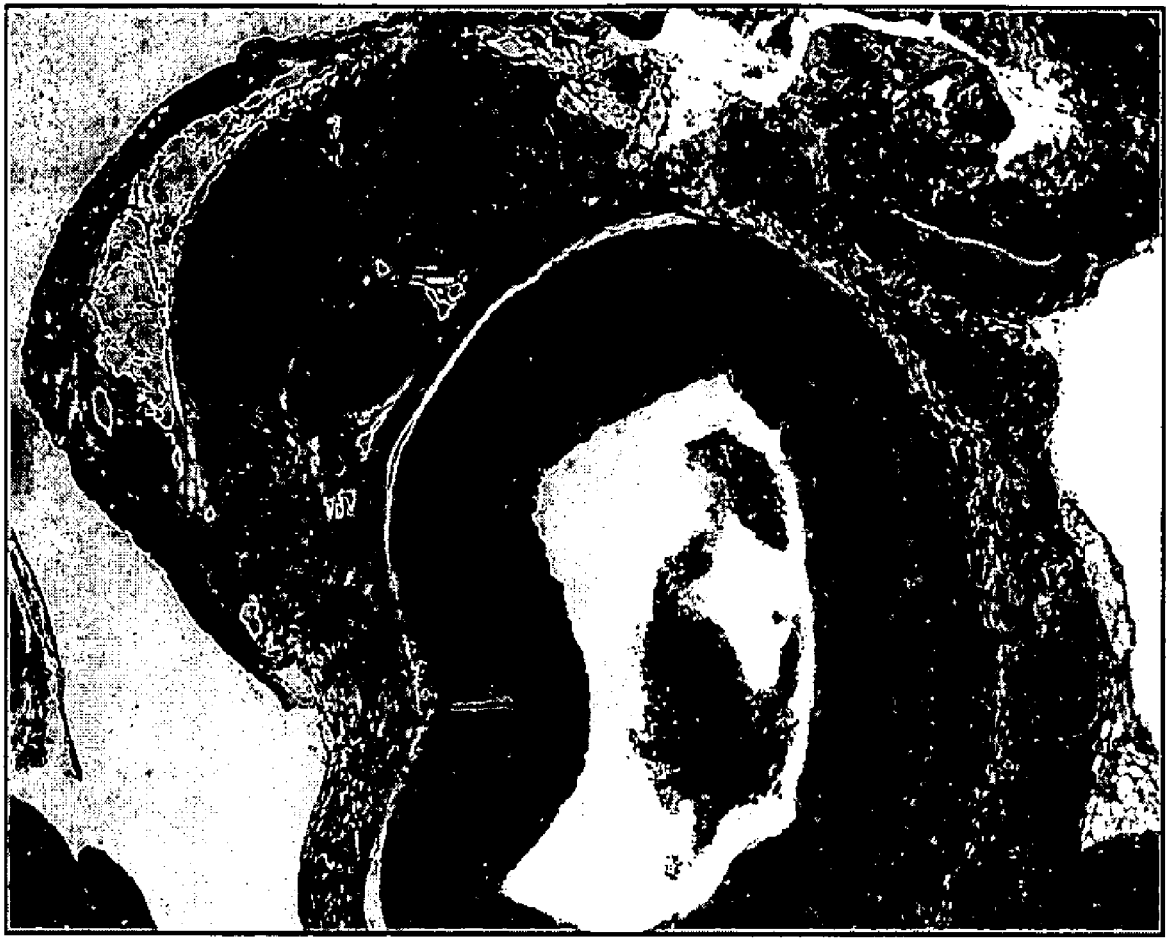

Warming blankets were used to keep the animal at normothermia as much as feasible. Vascular catheters were placed in the left common carotid artery for systemic arterial pressure monitoring and drawing blood samples. Another catheter was placed in a femoral vein for infusion of bacteria. A pulmonary arterial catheter was inserted via the right external jugular vein and positioned in the pulmonary artery for measurement of pulmonary arterial pressure and cardiac output. Animals were subjected to a lateral flank incision made 2-5 inches from the spleen in which the splenic nerve was isolated near the splenic hilus. A cuff electrode (FIG. 16) was placed around the isolated branches of the splenic nerve, including some branches of the vasculature and surrounding connective tissue. FIG. 17 demonstrates the surgical approach (FIG. 17 A.), the splenic nerve insitu (FIG. 17 B an C), and the histology of the nerve following the full procedure (FIG. 17 D). During each procedure, effort was made to consistently place electrode wires around a splenic nerve bundle at its location closest to the splenic hilus. Consistent electrode placement/content was confirmed during necropsy via gross pathology and histology analysis.

Lipopolysaccharide (*Escherichia coli* 0111:B4; Sigma Chemical Co, St. Louis, Mo.). Sepsis was induced by continuous i.v. infusion of *Escherichia coli* (*E. coli*) Lipopolysaccharide in saline solution 5 μg/kg/hr for two hours via a 12 cc leur-lock syringe and an infusion pump with catheter.

To determine whether direct stimulation of sympathetic nerve activity might suppress the systemic inflammatory response to endotoxin, splenic nerve activity was stimulated by application of constant voltage stimuli during the administration of a lethal LPS dose and for two hours following LPS administration. Animals either received endotoxin+ electrical stimulation, electrical stimulation alone, or endotoxin alone. Animals that received endotoxin alone underwent cuff electrode placement but the stimulator did not get turned on at anytime during the procedure. Electrical stimulation of the splenic nerve was achieved by a Medtronic test stimulator Model 3625. The cuff electrode was attached to the stimulator via alligator clip attaching the connector pin. Approximately 450 μsec wide pulses and burst frequencies of about 10 Hz were used at 10 Volts.

Arterial blood was collected at baseline and at 30 minute intervals for 8 hours following initial bacterial infusion. Blood samples were drawn from the arterial line for cytokine later analysis. Blood samples were allowed to clot for at least 30 minutes before centrifuging for 10 minutes at 2200 rpm. Serum was removed, aliquoted and stored in −20° C. freezer. Determination of cytokine levels was preformed according to the protocols included in the commercially available ELISA kits for Tumor Necrosis Factor-alpha (TNF-a), interleukin (IL)-1β, IL-6 and IL-10 (R&D Systems, Minneapolis Minn.).

Animals were euthanized immediately following the procedure following the AVMA Panel of 2000 guidelines.

Results

After 4 hours of stimulation at various frequencies (1-120 Hz) the artery and nerves remain intact. This is demonstrated by the histological evidence shown in FIG. 17D. This, together with observations made during necropsy suggest that stimulating the splenic nerve at various frequency, for varying periods of time does not adversely effect the splenic nerve tissue, surrounding tissue or vital organs.

Figure 18:
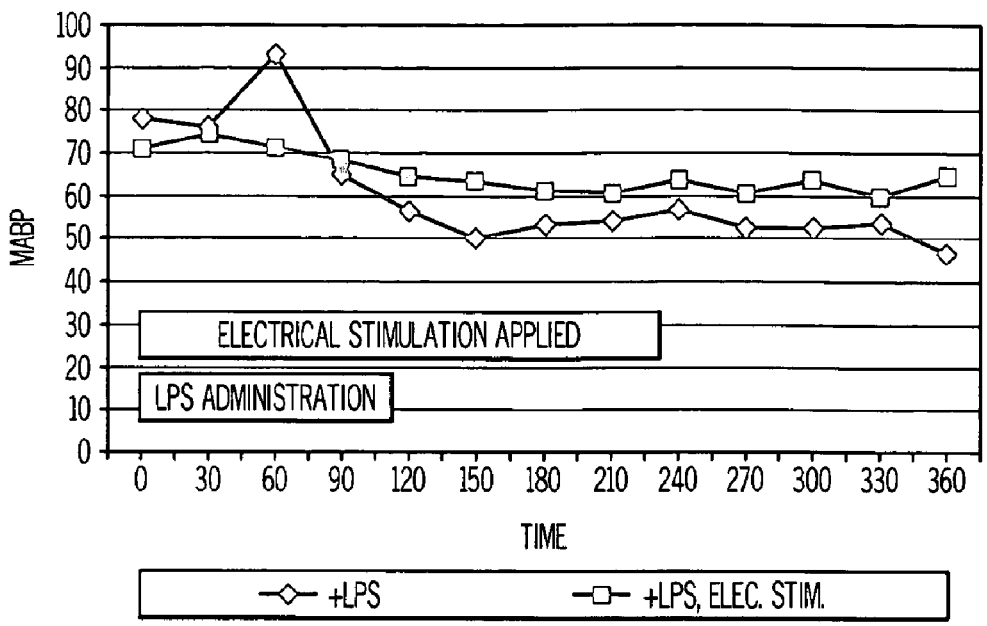
FIG. 18 is a graph demonstrating the effects of electrical stimulation of the splenic nerve on LPS-induced mean arterial blood pressure (MABP)

To determine if the electrical stimulation of the splenic nerve is safe, mean arterial blood pressures were measured throughout the study. MABP were compared between stimulated and non-stimulated septic animals. FIG. 18 shows this comparison. All data are expressed as % MABP from baseline. Electrical stimulation did not significantly affect MABP. Additionally, cardiac output was not significantly altered by electrical stimulation. Together, these data suggest that electrical stimulation applied to the splenic nerve does not adversely affect cardiac physiology. It is therefore believed that stimulation of the splenic nerve will be safe in both acute and chronic situations.

Figure 19A:
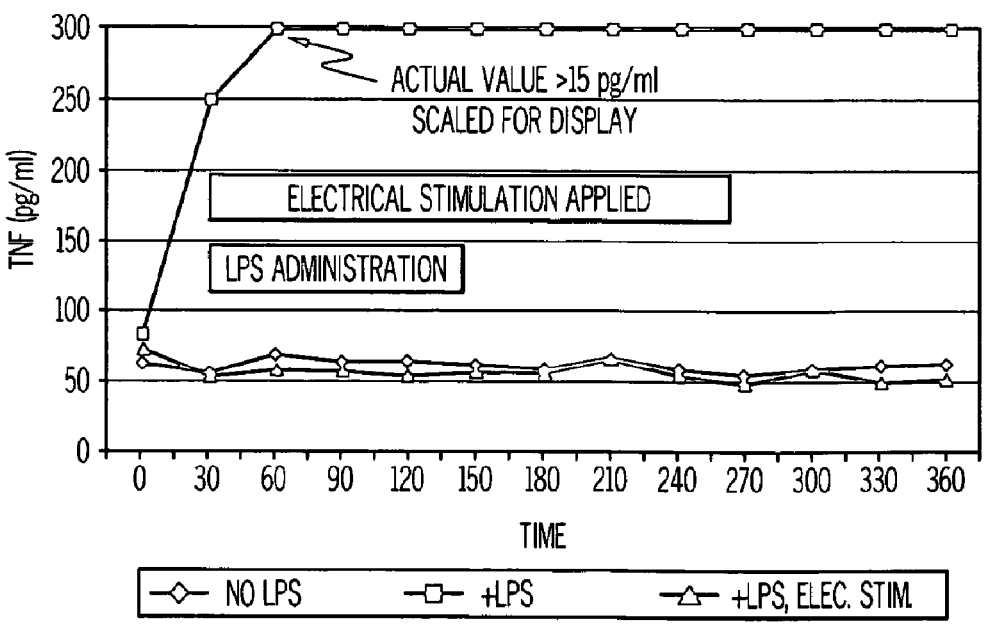
FIG. 19 A-C are graphs demonstrating the effects of electrical stimulation of the splenic nerve on LPS-induced pro inflammatory cytokine production.
Figure 19B:
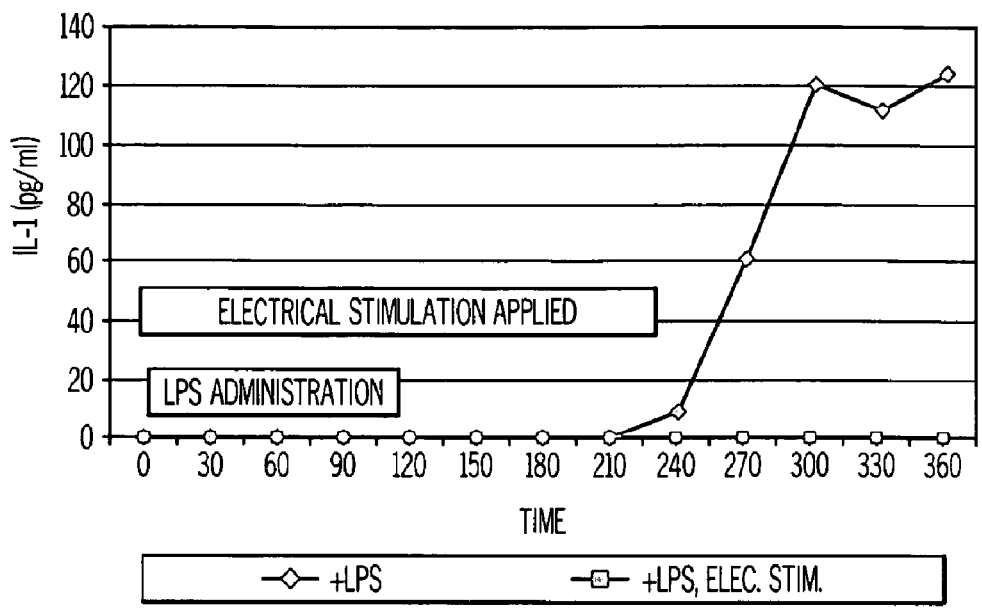
Figure 19C:
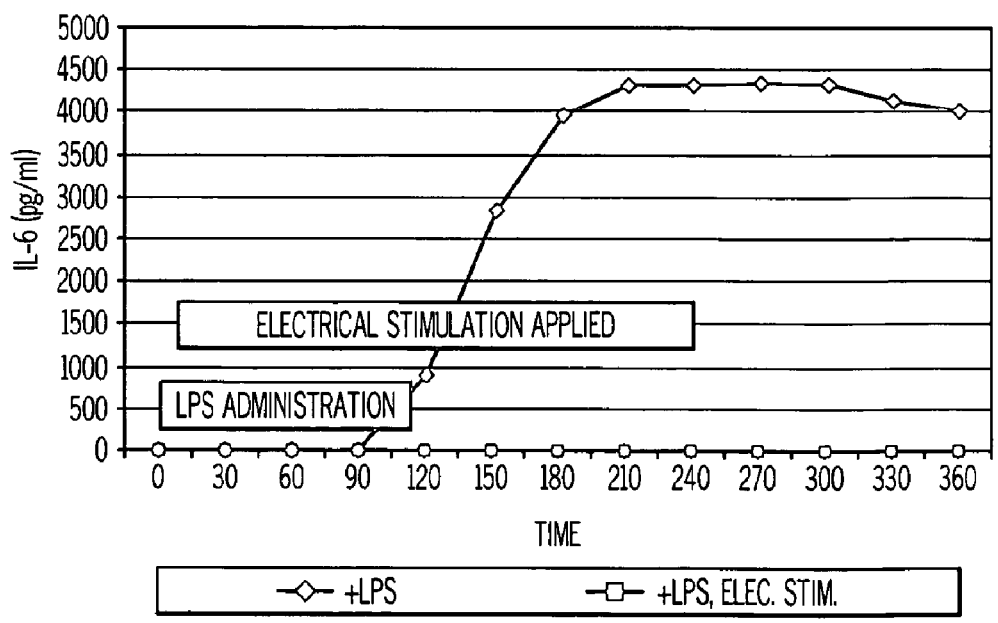

As shown in FIG. 19 (A-C), the results establish that electrical stimulation of the splenic nerve bundle significantly attenuates the LPS induced increase in serum TNF, IL-1 and IL-6 levels respectively. Preliminary evidence demonstrates that electrical stimulation of the splenic nerve also affects anti-inflammatory cytokines such as IL-10.

Figure 20:
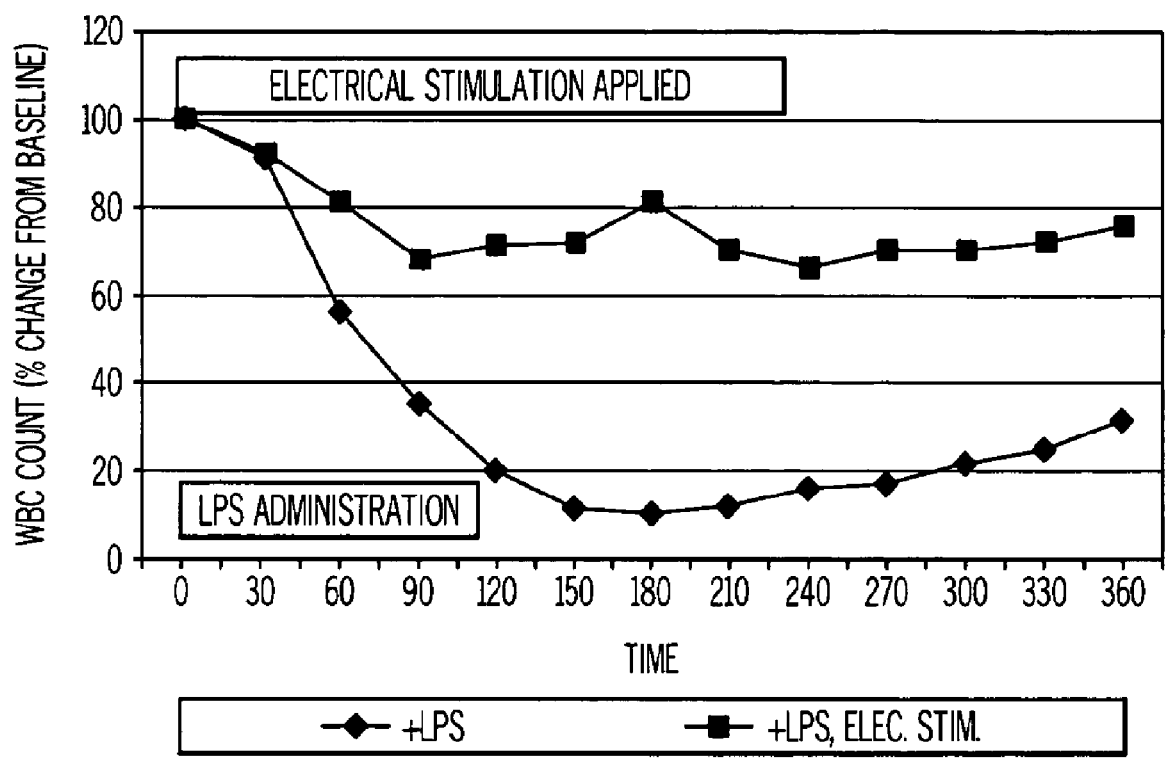
FIG. 20 is a graph demonstrating the effect of electrical stimulation of the splenic nerve on the LPS-induced reduction in white blood cell (WBC) count.

As shown in FIG. 20, the results establish that electrical stimulation of the splenic nerve bundle rescues the LPS-induced reduction in white blood cell count.

Discussion

Considered together, these observations indicate that stimulation of the splenic nerve activity downregulates systemic TNF production and the development of shock and inflammatory sequlea during lethal endotoxemia. Splenic nerve stimulation significantly attenuated the development of LPS-induced hypotension (shock) in pigs exposed to lethal doses of endotoxin. A therapy such as electrical stimulation of the splenic nerve that is capable of modulating systemic levels of TNF has broad therapeutic potential.

The data demonstrate that electrical stimulation of the splenic nerve is safe in that there is no adverse effect on cardiac physiology. This is a distinction from stimulation of the parasympathetics, specifically the vagus nerve. Stimulation of the vagus nerve often exerts negative effects on cardiac physiology.

Furthermore, stimulation of the splenic nerve was able to maintain the WBC count at a level of 75-85% of baseline. This brings the potential for therapy for a multitude of disorders that are characterized by a disturbance in WBC count. The effectiveness of stimulation of sympathetic nerve such as the splenic nerve in this exemplary embodiment where stimulation therapy was applied acutely indicates that therapy which includes stimulation of a sympathetic nervous system may also be beneficial of therapy for chronic disorders.

What is claimed is:

1. A method for inhibiting release of a proinflammatory mediator from a mammalian cell, the method comprising:
   identifying a mammalian subject suffering from, or at risk for, a disease or disorder mediated by a proinflammatory mediator; and
   applying a stimulation signal to the subject in an amount effective to inhibit the release of the proinflammatory mediator, wherein the stimulation signal is directly applied to a splenic nerve, a splenic neurovascular bundle, a periarterial splenic nerve, splenic peritoneum, splenic tissue, celiac plexus surrounding a celiac artery, a celiac ganglion, an aorticorenal ganglion, a greater thoracic splanchnic nerve, a lesser thoracic splanchnic nerve, a least thoracic splanchinc nerve or a combination thereof.

2. The method of claim 1, wherein the proinflammatory mediator is a pro-inflammatory cytokine.

3. The method of claim 2, wherein the pro-inflammatory cytokine is selected from the group consisting of tumor necrosis factor alpha (TNFα); interleukin (IL)-1α; IL-1β; IL-2; IL-5; IL-6; IL-8; IL-15; IL-18; interferon (IFN-γ); platelet-activating factor (PAF); Thromboxane; soluble adhesion molecules; vasoactive neuropeptides; phospholipase A2; Plasminogen activator inhibitor (PAI-1); Free radical generation; Neopterin; CD14; prostacyclin; Neutrophil elastase; Protein kinase; Monocyte chemotactic proteins 1 and 2 (MCP-1, MCP-2); macrophage migration inhibitory factor (MIF); and high mobility group box protein 1 (HMGB-1).

4. The method of claim 2, wherein the proinflammatory cytokine is selected from the group consisting of TNF-α; HMGB-1; IL-1; and IL-6.

5. The method of claim 2, wherein the proinflammatory cytokine is TNF-α.

6. The method of claim 1, wherein the pro-inflammatory mediator is a chemokine.

7. The method of claim 1, wherein the disease or disorder is selected from the group consisting of appendicitis, peptic, gastric and duodenal ulcers, peritonitis, pancreatitis, pseudomembranous colitis, acute ulcerative colitis, chronic ulcerative colitis and ischemic colitis, diverticulitis, epiglottitis, achalasia, cholangitis, cholecystitis, hepatitis, nosicomial infection, Crohn's disease, inflammatory bowel disease, enteritis, Whipple's disease, diabetes, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pelvic inflammatory disease, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, urticaria, warts, wheals, vasulitis, cardiovascular disease, angiitis, endocarditis, arteritis, atherosclerosis, thrombophlebitis, pericarditis, myocarditis, myocardial ischemia, periarteritis nodosa, rheumatic fever, rheumatoid arthritis, Alzheimer's disease, coeliac disease, congestive heart failure, adult respiratory distress syndrome, meningitis, encephalitis, multiple sclerosis, cerebral infarction, cerebral embolism, Guillane-Barre syndrome, neuritis, neuralgia, spinal cord injury, paralysis, uveitis, arthritides, arthralgias, osteomyelitis, fasciitis, Paget's disease, gout, periodontal disease, rheumatoid arthritis, synovitis, Sjogren's syndrome, myasthenia gravis, thryoiditis, systemic lupus erythematosus, lupus erythematosus, Addison's disease, pernicious anemia, Goodpasture's syndrome, Behcets's syndrome, allograft rejection, graft-versus-host disease, Type I diabetes, ankylosing spondylitis, Berger's disease, Type I diabetes, ankylosing spondylitis, spinal cord injury, Retier's syndrome, Graves disease, and Hodgkins disease.

8. The method of claim 1, wherein the disease or disorder is selected from the group consisting of endotoxic shock, appendicitis, peptic, gastric and duodenal ulcers, peritonitis, pancreatitis, inflammatory bowel disease, acute ulcerative colitis, chronic ulcerative colitis, ischemic colitis, hepatitis, nosicomial infection, Crohn's disease, diabetes, asthma, allergy, anaphylactic shock, arteriosclerosis, organ ischemia, reperfusion injury, organ necrosis, sepsis, septicemia, cachexia, septic abortion, disseminated bacteremia, burns, rheumatoid arthritis, Alzheimer's disease, coeliac disease, congestive heart failure, adult respiratory distress syndrome, cardiovascular disease, multiple sclerosis, diabetes, spinal cord injury, allograft rejection and graft-versus-host disease.

9. The method of claim 1, wherein applying the stimulation signal comprises applying the stimulation signal to a splenic nerve.

10. The method of claim 9, wherein applying the stimulation signal to the splenic nerve comprises applying the stimulation signal to a substantially fully dissected splenic nerve or nerve bundle.

11. The method of claim 1, wherein applying the stimulation signal further comprises applying the stimulation signal to a celiac plexus surrounding a celiac artery.

12. The method of claim 1, wherein applying the stimulation signal comprises applying the stimulation signal to a splenic neurovascular bundle.

13. The method of claim 1, wherein applying the stimulation signal comprises applying the stimulation signal to a periarterial splenic nerve.

14. The method of claim 1, wherein applying the stimulation signal comprises applying the stimulation signal to a splenic peritoneum.

15. The method of claim 1, wherein applying the stimulation signal further comprises applying the stimulation signal to a celiac ganglion.

16. The method of claim 1, wherein applying the stimulation signal further comprises applying the stimulation signal to an aorticorenal ganglion.

17. The method of claim 1, wherein applying the stimulation signal further comprises applying the stimulation signal to a greater thoracic splanchnic nerve.

18. The method of claim 1, wherein applying the stimulation signal further comprises applying the stimulation signal to a lesser thoracic splanchnic nerve.

19. The method of claim 1, wherein applying the stimulation signal further comprises applying the stimulation signal to a least thoracic splanchinc nerve.

20. The method of claim 1, further comprising stimulating a vagus nerve.

\* \* \* \* \*